(12) United States Patent
Britto et al.

(10) Patent No.: US 8,591,458 B2
(45) Date of Patent: Nov. 26, 2013

(54) PUMPING BREAST MILK

(75) Inventors: James J. Britto, Westport, MA (US); Richard M. Foley, Medfield, MA (US); Brian R. D'Amelio, Maynard, MA (US); Thomas A. Hagerty, Somerville, MA (US); Bryan R. Hotaling, Acton, MA (US); Jon R. Rossman, Chelmsford, MA (US); James R. Varney, Medford, MA (US)

(73) Assignee: Tomy International, Inc., Dyersville, IA (US)

( * ) Notice: Subject to any disclaimer, the term of this patent is extended or adjusted under 35 U.S.C. 154(b) by 1001 days.

(21) Appl. No.: 10/866,485

(22) Filed: Jun. 11, 2004

(65) Prior Publication Data

US 2004/0249340 A1    Dec. 9, 2004

Related U.S. Application Data

(63) Continuation of application No. 10/135,288, filed on Apr. 30, 2002, now Pat. No. 6,749,582.

(51) Int. Cl.
    *A61M 1/06*    (2006.01)

(52) U.S. Cl.
    USPC .................................. 604/74; 604/75; 604/76

(58) Field of Classification Search
    USPC ...................................................... 604/74–76
    See application file for complete search history.

(56) References Cited

U.S. PATENT DOCUMENTS

| | | |
|---|---|---|
| 316,584 A | 4/1885 | Turner |
| 532,236 A | 1/1895 | Hardesty |
| 684,078 A | 10/1901 | Martin |
| 823,316 A | 6/1906 | Andersen |
| 956,325 A | 4/1910 | Fey |
| 975,047 A | 11/1910 | Klein et al. |
| 1,113,942 A | 10/1914 | Anderson |
| 1,184,293 A | 5/1916 | Zeratsky |
| 1,184,631 A | 5/1916 | De Leon |
| 1,259,309 A | 3/1918 | Somers |

(Continued)

FOREIGN PATENT DOCUMENTS

| | | |
|---|---|---|
| CA | 2115824 | 8/1994 |
| CA | 2215368 | 2/1996 |

(Continued)

OTHER PUBLICATIONS

Merriam-Webster Online defeiniton of "port".*

*Primary Examiner* — Kevin C Sirmons
*Assistant Examiner* — Edelmira Bosques
(74) *Attorney, Agent, or Firm* — Michael Best & Friedrich LLP

(57) ABSTRACT

A breast pump provides multiple orientations of the pumping lever with respect to the breast shield. A breast pump includes a liner extending from the breast shield, through the suction chamber, and out of the suction chamber, which liner shields other components of the pump from contamination by the flow of milk through the pump during pumping operation. A breast pumping device includes a pumping lever for manually providing a cyclical vacuum within the suction chamber and an external pumping source, connected to the suction bell, that the user can activate to provide a cyclical vacuum within the suction chamber. A breast pump provides a smaller change in the grip width from when the lever is fully-extended to when the lever is fully-retracted, allowing more comfortable manual pumping.

37 Claims, 19 Drawing Sheets

(56) References Cited

U.S. PATENT DOCUMENTS

| | | | |
|---|---|---|---|
| 1,460,927 | A | 7/1923 | Thompson et al. |
| 1,596,520 | A | 8/1926 | Eskholme et al. |
| 1,644,257 | A | 10/1927 | Lasker |
| 1,670,610 | A | 5/1928 | Colby |
| 2,060,063 | A | 11/1936 | Frimand |
| 2,222,811 | A | 11/1940 | Dinesen |
| 2,419,795 | A | 4/1947 | Saunders |
| 2,522,108 | A | 9/1950 | Flagg |
| 2,542,505 | A | 2/1951 | Gascoigne |
| 2,545,857 | A | 3/1951 | Perkins et al. |
| 3,233,607 | A | 2/1966 | Bolie |
| 3,238,937 | A | 3/1966 | Stein |
| 3,382,867 | A | 5/1968 | Reaves |
| 3,587,567 | A | 6/1971 | Schiff |
| 3,738,363 | A | 6/1973 | Lunas et al. |
| 3,782,385 | A | 1/1974 | Loyd |
| 3,797,734 | A | 3/1974 | Fleury et al. |
| 3,822,703 | A | 7/1974 | Davisson |
| 3,830,238 | A | 8/1974 | Kurtz et al. |
| 3,911,920 | A | 10/1975 | Susinn |
| 3,931,795 | A | 1/1976 | Duncan |
| 3,977,405 | A | 8/1976 | Yanase |
| 3,990,816 | A | 11/1976 | Kohler et al. |
| 4,249,481 | A | 2/1981 | Adams |
| 4,263,912 | A | 4/1981 | Adams |
| 4,311,141 | A | 1/1982 | Diamond |
| 4,323,067 | A | 4/1982 | Adams |
| 4,486,157 | A | 12/1984 | Hayashi |
| 4,501,585 | A | 2/1985 | Friedman |
| 4,573,969 | A | 3/1986 | Schlensog et al. |
| 4,583,970 | A | 4/1986 | Kirchner |
| 4,607,596 | A | 8/1986 | Whittlestone et al. |
| 4,634,430 | A | 1/1987 | Polaschegg |
| 4,673,388 | A | 6/1987 | Schlensog et al. |
| 4,680,028 | A | 7/1987 | Stuart |
| 4,705,504 | A | 11/1987 | Viers |
| 4,759,747 | A | 7/1988 | Aida et al. |
| 4,772,262 | A | 9/1988 | Grant et al. |
| 4,775,366 | A | 10/1988 | Rosenblatt |
| 4,794,915 | A | 1/1989 | Larsson |
| 4,799,922 | A | 1/1989 | Beer et al. |
| 4,799,924 | A | 1/1989 | Rosenblatt |
| 4,799,925 | A | 1/1989 | Rosenblatt |
| 4,813,932 | A * | 3/1989 | Hobbs ............... 604/74 |
| 4,857,051 | A | 8/1989 | Larsson |
| 4,883,464 | A | 11/1989 | Morifuki |
| 4,898,578 | A | 2/1990 | Rubalcaba, Jr. |
| 4,929,229 | A | 5/1990 | Larsson |
| 4,941,433 | A | 7/1990 | Hanauer |
| 4,950,236 | A | 8/1990 | Wilson |
| 4,961,726 | A | 10/1990 | Richter |
| 4,964,851 | A | 10/1990 | Larsson |
| 5,007,899 | A | 4/1991 | Larsson |
| 5,009,638 | A | 4/1991 | Riedweg et al. |
| 5,049,126 | A | 9/1991 | Larsson |
| 5,076,769 | A | 12/1991 | Shao |
| 5,100,406 | A | 3/1992 | Panchula |
| 5,104,374 | A | 4/1992 | Bishko et al. |
| 5,178,095 | A | 1/1993 | Mein |
| 5,218,924 | A | 6/1993 | Thompson et al. |
| 5,295,957 | A * | 3/1994 | Aida et al. ............... 604/74 |
| 5,304,129 | A | 4/1994 | Forgach |
| 5,356,398 | A | 10/1994 | Willis |
| 5,358,476 | A * | 10/1994 | Wilson ............... 604/74 |
| 5,368,583 | A | 11/1994 | Fleury |
| 5,514,166 | A | 5/1996 | Silver et al. |
| 5,542,921 | A | 8/1996 | Meyers et al. |
| 5,547,470 | A | 8/1996 | Johnson et al. |
| 5,571,084 | A | 11/1996 | Palmer |
| 5,586,518 | A | 12/1996 | Carrano |
| 5,590,648 | A | 1/1997 | Mitchell et al. |
| 5,601,531 | A | 2/1997 | Silver |
| 5,616,125 | A | 4/1997 | Jelks |
| 5,676,525 | A | 10/1997 | Berner et al. |
| 5,691,932 | A | 11/1997 | Reiner et al. |
| 5,720,722 | A | 2/1998 | Lockridge |
| 5,749,850 | A | 5/1998 | Williams et al. |
| 5,776,098 | A | 7/1998 | Silver et al. |
| 5,810,772 | A | 9/1998 | Niederberger |
| 5,843,029 | A | 12/1998 | Bachman et al. |
| D406,348 | S | 3/1999 | Koehnke |
| 5,885,246 | A | 3/1999 | Ford |
| 5,902,267 | A | 5/1999 | Medo |
| 5,941,847 | A | 8/1999 | Huber et al. |
| 5,947,923 | A | 9/1999 | Uehara et al. |
| 5,954,690 | A | 9/1999 | Larsson |
| 6,045,529 | A | 4/2000 | Nuesch |
| 6,050,432 | A | 4/2000 | Koehnke |
| 6,090,065 | A | 7/2000 | Giles |
| 6,110,140 | A | 8/2000 | Silver |
| 6,116,780 | A | 9/2000 | Young et al. |
| 6,139,521 | A | 10/2000 | Larsson |
| 6,152,896 | A | 11/2000 | Bachman et al. |
| 6,257,847 | B1 | 7/2001 | Silver et al. |
| 6,270,474 | B1 | 8/2001 | Nuesch |
| 6,290,671 | B1 | 9/2001 | Niederberger |
| 6,299,594 | B1 | 10/2001 | Silver |
| 6,314,315 | B1 | 11/2001 | Hung et al. |
| 6,328,082 | B1 | 12/2001 | Lafond |
| 6,328,709 | B1 | 12/2001 | Hung et al. |
| 6,355,012 | B1 | 3/2002 | Nuesch |
| 6,379,327 | B2 | 4/2002 | Lundy |
| 6,383,163 | B1 | 5/2002 | Kelly et al. |
| 6,387,072 | B1 | 5/2002 | Larsson et al. |
| 6,423,030 | B1 | 7/2002 | Silver |
| 6,427,475 | B1 | 8/2002 | DeFelice et al. |
| 6,440,100 | B1 | 8/2002 | Prentiss |
| 6,461,324 | B1 * | 10/2002 | Schlensog ............... 604/74 |
| 6,481,986 | B1 | 11/2002 | Silver et al. |
| 6,497,677 | B2 | 12/2002 | Silver |
| 6,500,143 | B2 | 12/2002 | Suh |
| 6,547,756 | B1 | 4/2003 | Greter et al. |
| 6,575,202 | B2 | 6/2003 | Lafond |
| 6,579,258 | B1 | 6/2003 | Atkin et al. |
| 6,585,686 | B2 | 7/2003 | Cloud |
| 6,610,024 | B1 | 8/2003 | Benatti |
| 6,616,000 | B1 | 9/2003 | Renz |
| 6,629,936 | B2 | 10/2003 | Hung et al. |
| 6,638,727 | B2 | 10/2003 | Hung et al. |
| 6,652,484 | B1 | 11/2003 | Hunckler et al. |
| 6,663,587 | B2 | 12/2003 | Silver et al. |
| D484,970 | S | 1/2004 | Renz et al. |
| 6,673,036 | B1 | 1/2004 | Britto |
| 6,673,037 | B1 | 1/2004 | Silver |
| 6,676,610 | B2 | 1/2004 | Morton et al. |
| 6,676,631 | B1 | 1/2004 | Greter |
| D486,223 | S | 2/2004 | Robson et al. |
| 6,689,073 | B2 | 2/2004 | Quay |
| 6,699,213 | B1 | 3/2004 | Annis et al. |
| 6,702,167 | B2 | 3/2004 | Annis |
| 6,705,108 | B2 | 3/2004 | Defelice et al. |
| 6,705,920 | B1 | 3/2004 | Engel |
| 6,706,012 | B2 | 3/2004 | McKendry et al. |
| 6,712,785 | B2 | 3/2004 | Morton et al. |
| 6,732,773 | B2 | 5/2004 | Renz |
| 6,740,075 | B2 | 5/2004 | Lebel et al. |
| D491,363 | S | 6/2004 | Renz et al. |
| 6,749,582 | B2 | 6/2004 | Britto et al. |
| 6,750,037 | B2 | 6/2004 | Adair et al. |
| 6,763,857 | B2 | 7/2004 | Brown |
| 6,764,377 | B2 | 7/2004 | Gillan |
| 6,779,638 | B2 | 8/2004 | Renz et al. |
| 6,840,918 | B1 | 1/2005 | Britto et al. |
| 6,866,558 | B2 | 3/2005 | Luciano et al. |
| 6,884,229 | B2 | 4/2005 | Renz |
| 6,887,210 | B2 | 5/2005 | Quay |
| 6,887,218 | B2 | 5/2005 | Warburton |
| D507,111 | S | 7/2005 | Renz et al. |
| 6,921,379 | B2 | 7/2005 | Greter et al. |
| 6,932,780 | B2 | 8/2005 | Kozersky |
| 6,932,790 | B2 | 8/2005 | McKendry et al. |
| 6,964,651 | B1 | 11/2005 | McKendry |
| 6,974,361 | B2 | 12/2005 | Cravaack et al. |
| 6,974,439 | B1 * | 12/2005 | McKendry ............... 604/74 |

(56) References Cited

U.S. PATENT DOCUMENTS

| | | |
|---|---|---|
| 6,974,440 B2 | 12/2005 | Silver |
| 6,988,930 B2 | 1/2006 | Gillan |
| 6,997,897 B1 | 2/2006 | Silver et al. |
| 6,999,840 B2 | 2/2006 | Brezina et al. |
| 7,004,339 B2 | 2/2006 | Renz |
| 7,029,454 B2 | 4/2006 | Watanabe |
| 7,029,456 B2 | 4/2006 | Ware et al. |
| 7,101,350 B2 | 9/2006 | Ytteborg |
| 7,150,346 B2 | 12/2006 | Renz et al. |
| 7,160,273 B2 | 1/2007 | Greter et al. |
| 7,166,087 B2 | 1/2007 | Silver et al. |
| 7,201,735 B2 | 4/2007 | Atkin et al. |
| 7,223,255 B2 | 5/2007 | Myers et al. |
| 7,255,681 B1 | 8/2007 | Silver et al. |
| 7,267,662 B1 | 9/2007 | Kirchner |
| 7,311,106 B1 | 12/2007 | Burton |
| 7,326,184 B2 | 2/2008 | Rollin |
| 7,354,418 B2 | 4/2008 | Lee et al. |
| 7,357,782 B2 | 4/2008 | Rollin et al. |
| 7,381,197 B2 | 6/2008 | Kelly et al. |
| 7,396,339 B2 | 7/2008 | Britto et al. |
| 7,396,340 B2 | 7/2008 | Onuki et al. |
| 7,413,557 B2 | 8/2008 | Samson et al. |
| 7,440,786 B2 | 10/2008 | Hockersmith et al. |
| 7,471,994 B2 | 12/2008 | Ford et al. |
| 7,472,797 B2 | 1/2009 | Ostrowski |
| 7,479,125 B2 | 1/2009 | Tashiro |
| 7,559,915 B2 | 7/2009 | Dao et al. |
| 7,569,031 B2 | 8/2009 | Britto |
| 7,575,557 B2 | 8/2009 | Morton et al. |
| 7,611,399 B2 | 11/2009 | Brigham |
| 7,641,629 B2 | 1/2010 | Yuen |
| 7,662,127 B2 | 2/2010 | Silver et al. |
| 7,682,334 B2 | 3/2010 | Greter et al. |
| 7,713,230 B2 | 5/2010 | Kataoka et al. |
| 7,727,182 B2 | 6/2010 | Silver |
| 7,749,188 B2 | 7/2010 | Tashiro et al. |
| 7,758,540 B2 | 7/2010 | Yamashita et al. |
| 7,766,865 B2 | 8/2010 | Rollin |
| 7,780,201 B2 | 8/2010 | Luzbetak et al. |
| 7,785,305 B2 | 8/2010 | Myers et al. |
| 7,789,865 B2 | 9/2010 | Myers et al. |
| 7,789,965 B2 | 9/2010 | Matsushita et al. |
| 7,806,855 B2 | 10/2010 | Kliegman et al. |
| 7,811,248 B2 | 10/2010 | Bjorge |
| 7,819,839 B2 | 10/2010 | Gillan |
| 7,824,362 B2 | 11/2010 | Annis et al. |
| 7,824,363 B2 | 11/2010 | Myers |
| 7,833,190 B1 | 11/2010 | Hall |
| 7,835,230 B1 | 11/2010 | Chang |
| 7,875,000 B2 | 1/2011 | Krebs et al. |
| 7,887,507 B2 | 2/2011 | Shemesh et al. |
| 7,912,674 B2 | 3/2011 | Killoren Clark et al. |
| 7,945,452 B2 | 5/2011 | Fathallah et al. |
| 7,972,297 B2 | 7/2011 | Bryan et al. |
| 7,988,661 B2 | 8/2011 | Silver et al. |
| 8,052,634 B2 | 11/2011 | Thommen et al. |
| 8,052,635 B1 | 11/2011 | Kelly et al. |
| 8,057,425 B1 | 11/2011 | Myers et al. |
| 8,070,715 B2 | 12/2011 | Quackenbush et al. |
| 8,070,716 B2 | 12/2011 | Sutrina et al. |
| 8,070,724 B2 | 12/2011 | Attolini et al. |
| 8,075,516 B2 | 12/2011 | Pfenniger et al. |
| 8,096,824 B2 | 1/2012 | Luzbetak et al. |
| 8,096,970 B2 | 1/2012 | Annis et al. |
| 8,100,854 B2 | 1/2012 | Vogelin et al. |
| 8,109,901 B2 | 2/2012 | Bryan et al. |
| 8,118,772 B2 | 2/2012 | Dao et al. |
| 8,137,305 B2 | 3/2012 | Kelly et al. |
| 8,142,393 B2 | 3/2012 | Myers |
| 8,152,754 B2 | 4/2012 | Silver |
| 8,167,833 B2 | 5/2012 | Tashiro |
| 8,187,219 B1 | 5/2012 | Chiang |
| 8,187,227 B2 | 5/2012 | Luzbetak et al. |
| 8,192,396 B2 | 6/2012 | Annis et al. |
| 8,216,178 B2 | 7/2012 | Thommen |
| 8,216,179 B2 | 7/2012 | Bosshard et al. |
| 8,262,606 B2 | 9/2012 | Greter et al. |
| 2001/0038799 A1 | 11/2001 | Silver et al. |
| 2002/0062103 A1 | 5/2002 | Larsson et al. |
| 2002/0072701 A1 | 6/2002 | Nuesch |
| 2002/0198489 A1* | 12/2002 | Silver et al. ............ 604/74 |
| 2003/0069215 A1 | 4/2003 | Greter et al. |
| 2003/0139702 A1 | 7/2003 | Renz et al. |
| 2003/0149398 A1 | 8/2003 | Renz et al. |
| 2004/0024352 A1 | 2/2004 | Renz et al. |
| 2004/0127845 A1 | 7/2004 | Renz et al. |
| 2005/0154349 A1 | 7/2005 | Renz et al. |
| 2005/0159656 A1 | 7/2005 | Hockersmith et al. |
| 2005/0159701 A1 | 7/2005 | Conaway |
| 2005/0283112 A1 | 12/2005 | Britto |
| 2006/0195064 A1 | 8/2006 | Plahey et al. |
| 2007/0135761 A1 | 6/2007 | Cheng et al. |
| 2007/0161948 A1* | 7/2007 | Renz et al. ............ 604/74 |
| 2008/0090444 A1 | 4/2008 | Luzbetak et al. |
| 2008/0221495 A1 | 9/2008 | Steffens et al. |
| 2008/0243061 A1 | 10/2008 | Britto et al. |
| 2009/0227855 A1 | 9/2009 | Hill et al. |
| 2009/0254029 A1 | 10/2009 | Tashiro et al. |
| 2009/0270810 A1 | 10/2009 | Debelser et al. |
| 2010/0016789 A1 | 1/2010 | Bosshard et al. |
| 2010/0049119 A1 | 2/2010 | Norman et al. |
| 2010/0094078 A1 | 4/2010 | Weston |
| 2010/0100037 A1 | 4/2010 | Cozmi et al. |
| 2010/0228222 A1 | 9/2010 | Williams et al. |
| 2011/0060328 A1 | 3/2011 | Skwarek et al. |
| 2011/0144569 A1 | 6/2011 | Britton et al. |
| 2011/0172524 A1 | 7/2011 | Hidem et al. |
| 2011/0275984 A1 | 11/2011 | Biewer et al. |
| 2012/0029424 A1 | 2/2012 | Greter et al. |

FOREIGN PATENT DOCUMENTS

| | | |
|---|---|---|
| CA | 2487980 | 12/2003 |
| DE | 540934 | 12/1931 |
| DE | 2807646 | 8/1978 |
| DE | 3228725 | 2/1984 |
| EP | 0123269 | 10/1984 |
| EP | 0604070 | 6/1994 |
| EP | 0611578 | 8/1994 |
| FR | 599054 | 1/1926 |
| GB | 271857 | 10/1927 |
| GB | 762701 | 12/1956 |
| GB | 2082920 | 3/1982 |
| GB | 2127293 | 4/1984 |
| JP | 2001259023 | 9/2001 |
| NZ | 168234 | 9/1921 |
| SE | 158976 | 5/1957 |
| WO | 9011097 | 10/1990 |
| WO | 9634638 | 11/1996 |
| WO | 9705913 | 2/1997 |
| WO | 9944650 | 9/1999 |
| WO | 9951882 | 10/1999 |
| WO | 0041744 | 7/2000 |
| WO | 0041745 | 7/2000 |
| WO | 0057934 | 10/2000 |

* cited by examiner

PUMPING BREAST MILK

This is a continuation of U.S. patent application Ser. No. 10/135,288, filed Apr. 30, 2002, issued Jun. 15, 2004, as U.S. Pat. No. 6,749,582.

TECHNICAL FIELD

This invention relates to pumps for pumping breast milk.

BACKGROUND

Nursing mothers frequently use mechanized pumps to express milk from their breasts for bottle-feeding their infant children. Some such pumps are manually operated, in that the pumping action is motivated by reciprocating a piston or lever by hand, or compressing a flexible bulb. Often the pump lever is located directly on a structure that must be held against the breast while the lever is reciprocated. Other such pumps are electrically operated, and are generally considered less fatiguing than manual pumps. Between uses, careful cleaning is required to keep the pump components that come in contact with breast milk sanitary.

Pumped milk must typically be refrigerated if it will not be immediately consumed. It is common to store such milk in sanitized bottles or bags. Improvements to pump constructions and pumping methods are desired, for comfortable and sanitary use.

SUMMARY

According to one aspect of the invention, a manual breast pump includes a suction bell having an internal suction chamber, a breast shield extending from the suction bell for receiving a human breast, and manually operable pumping lever secured to the suction bell for generating a cyclical vacuum within the suction chamber. The pumping lever is repositionable to multiple orientations with respect to the breast shield, and can be operated in each of the orientations to generate suction chamber vacuum.

Such breast pumps may be configured to assume multiple configurations, allowing the user to select from among different orientations of the pumping lever with respect to the breast shield for creating a cyclic vacuum condition within the suction chamber of the breast pump. For example, the pump can permit different orientations that allow the user to switch between the use of her right and left hands during a given breast pumping session.

In some embodiments, the lever is attached to a fulcrum repositionably secured to the suction bell.

In some cases, the fulcrum is secured to a collar that is rotatably secured to the suction bell. In some such pumps, the suction bell and collar together define a positioning detent that secures the lever in at least one of the multiple orientations of the lever with respect to the breast shield.

In some embodiments of the pump, the collar is secured to the suction bell by tabs extending from the collar and lodging in an annular channel on the suction bell, allowing the collar to be rotated in the manner of a dial with respect to the suction bell. In some such pumps, cutouts in the suction bell channel allow the tabs of the collar to lodge within the channel.

In some embodiments, the breast pump contains a flexible diaphragm attached to the suction bell such that it is in hydraulic communication with the suction chamber. In some such pumps the lever can be connected to the flexible diaphragm for creation of the cyclical vacuum. In some cases, the lever is connected to a rigid plunger which in turn is attached to the flexible diaphragm. In some configurations the diaphragm is removable from the suction bell, and in some of those pumps the diaphragm is attached to a separate pumping bell that is itself removably attached to the suction bell. In some cases, the diaphragm is attached to a pumping bell and defines a pumping chamber that is in hydraulic communication with the suction chamber of the suction bell. Threads are provided on the pumping bell, in some instances, to cooperate with threads on the suction bell to secure the pumping bell to the suction bell, which threads in some pumps comprise a quarter-turn fastener.

In some embodiments, a tortuous conduit hydraulically connects the pumping and suction chambers. In some such pumps, the tortuous conduit is defined by external surfaces of the pumping and suction bells, a perforation in the pumping bell, and a perforation in the suction bell.

In some cases, the lever is operably connected to a piston, which piston is slidably disposed within a cylinder, which cylinder is in hydraulic communication with the suction chamber. Some such pumps include a flexible ring between the piston and the cylinder wall for providing a slidable seal.

In some pumps, the lever is secured to the suction bell such that suction chamber pressure decreases in each cycle with a forward motion of the lever, and increases in each cycle with a return motion of the lever.

In some cases a valve, adapted to drain pumped milk from the suction chamber, is attached to the suction bell. A milk receptacle is removably secured to the suction bell beneath the valve in some such pumps. And in some instances, the valve is configured to restrict flow into the suction chamber as pressure in the suction chamber is lowered by pumping. Preferably, the valve is configured to drain pumped milk from the suction chamber when weight of milk above the valve exceeds a predetermined amount with vacuum pressure released. The valve in some cases is a duckbill valve.

In some configurations, the suction bell has an outer surface that defines a recess, on a side of the suction bell opposite the pumping lever. In some such pumps, this recess, together with the pumping lever, defines a manual grip that a user can cyclically squeeze to operate the pump. In some cases the recess is a neck in the suction bell, and in some of those pumps the pumping lever is shaped to conform to the neck. Preferably, the manual grip has a grip width changing less than one inch (more preferably, less than ¾ of an inch) as the lever moves from a fully extended position to a fully retracted position.

Preferably, two of the multiple orientations define an adjustment range angle of at least forty-five degrees, more preferably, at least ninety degrees, and even more preferably, at least one-hundred and eighty degrees. In some cases, multiple positioning detents are defined between the lever and the suction bell, each detent corresponding to one of the multiple orientations.

According to another aspect of the invention, a breast pump includes a suction bell having an internal suction chamber, a breast shield extending from the suction bell for receiving a human breast, a valve attached to the suction bell that partially defines the suction chamber and is adapted to drain pumped milk from the suction chamber, and a removable, flexible liner, extending from within the breast shield, through the suction chamber, and out of the suction chamber through the valve, and defining a conduit for conducting pumped milk.

In some cases, the liner conducts pumped milk from the breast shield, through the suction chamber, and out of the suction chamber through the milk drainage valve for storage, while at the same time preventing contact between the pumped milk and those, and other, parts of the pump during normal operation. This can advantageously prevent parts of the pump other than the liner from contacting milk flow, simplifying cleaning and sterilization.

In some cases, the valve is configured to restrict flow into the suction chamber as pressure in the suction chamber is lowered by pumping. In some instances, the valves is a duckbill valve with one rigid bill and one flexible bill. Preferably, at least one bill is rigid and fixed in relation to the suction bell.

In some embodiments, the suction bell can be opened at a hinged joint to expose the suction chamber for liner insertion.

In many instances the pump is manually operable. For example, some embodiments have a manually operable pump lever secured to the suction bell for the user to generate a cyclical vacuum within the suction chamber.

In some cases, the liner defines a pouch external to the suction chamber for containing pumped milk. Some liners include a frangible section for separating the pouch from a remainder of the liner for milk storage. In some instances, the liner includes a pouch seal below the frangible section, for sealing milk within the pouch for milk storage. The pouch seal includes, in some instances, mating rib and groove fastener sections.

Preferably, the liner extends to a distal rim of the breast shield. Preferred liner materials include low-density polyethylene, for example.

According to still another aspect of the invention, a breast pumping device has a suction bell with an internal suction chamber, a breast shield extending from the suction bell and defining a receptacle for receiving a human breast, a hand-operable lever secured to the suction bell for a user to generate a cyclical vacuum within the suction chamber, a secondary vacuum cycling pump in hydraulic communication with the suction chamber through a length of flexible tubing, and a valve for switching between a hand pumping mode and a secondary vacuum cycling pumping mode. The valve is repositionable between a first position that restricts hydraulic communication between the secondary vacuum cycling pump and the suction chamber, and a second position enabling hydraulic communication between the secondary vacuum cycling pump and the suction chamber, for switching between a hand pumping mode and a secondary vacuum cycling pumping mode of the device.

Advantages of such a breast pump may include ready switching between a manual pumping mode and another pumping mode, such as in which an external pumping source (e.g., an electric pump or a foot-operated pump) is connected to the suction bell and provides the cyclical vacuum necessary to induce lactation.

Some such pumps include a first port for attaching to the flexible tubing so that when the valve is positioned at its second position and the flexible tubing is attached to the first port, the secondary vacuum cycling pump will in hydraulic communication with the suction chamber through the flexible tubing. And in some embodiments, the mechanical and hydraulic connection between the flexible tubing and the first port is accomplished through a fitting positioned between and attached to the flexible tubing and the first port.

In some embodiments, the valve is repositionable between a first position, a second position, and a third position, with the suction bell defining a second port for attaching to the flexible tubing, through which, when the valve is positioned at the third position and the flexible tubing is attached to the second port, the secondary vacuum cycling pump is in hydraulic communication with the suction chamber. In some such cases, a fitting is positioned between and attached to the flexible tubing and the second port. And in some such pumps, the first and second ports are oriented in opposite lateral directions. Preferably, the first and second ports are located on opposites sides of the suction bell from the perspective of the breast shield.

In some embodiments, the port-selection valve has a body, a portion of which is disposed within the suction bell and at least partially defines a conduit through which the secondary vacuum cycling pump and the suction chamber hydraulically communicate.

In some instances, the lever is secured to the suction bell for cyclical motion by the user in which suction chamber pressure decreases in each cycle with a forward motion of the lever, and increases in each cycle with a return motion of the lever.

In another aspect of the invention, the change in grip width of a breast pump, as measured from when the pumping lever is in its fully extended position to when the pumping lever is in its fully retracted position, is less than about three-quarters of an inch. Such an optimally low grip width change may provide increased comfort for women pumping milk from their breasts and reduce fatigue during manual pumping operation.

According to another aspect of the invention, a manual breast pump includes a suction bell defining an internal suction chamber and a pumping chamber, the suction and pumping chambers being in hydraulic communication via an aperture through an internal suction bell wall, the aperture positioned at an upper end of the suction chamber. The pump has a breast shield extending from the suction bell and defining a receptacle for receiving a human breast, with the receptacle being in hydraulic communication with the suction chamber via a port disposed below the aperture. A valve forms a lower extent of the suction chamber and is constructed to both inhibit air flow into the suction chamber and to drain pumped milk from the suction chamber. The pumping chamber forms a manually cyclable volume, such that when the pumping chamber is expanded a vacuum is created in the suction chamber, and when the pumping chamber is subsequently collapsed the vacuum is reduced. Notably, the aperture provides hydraulic communication between the pumping and suction chambers only through a tortuous air flow conduit requiring multiple flow direction changes between the pumping and suction chambers.

In some embodiments, one side of the pumping chamber is defined by a movable diaphragm that is operably connected to a manually displaceable pumping lever.

In some cases, the pumping chamber is defined within a cup-shaped cavity in the suction bell, with the cavity containing a diaphragm that generally conforms, in a relaxed state, to the shape of the cavity. The aperture and air flow conduit are preferably disposed at a lower extent of the cavity.

In some constructions, the air flow conduit comprises an annular channel within the internal suction bell wall, with the annular channel in communication with the suction chamber at one rotational position along the channel via the aperture, and in communication with the pumping chamber via a port extending from the channel at another rotational position. Preferably, the rotational positions along the channel corresponding to the aperture and the hole are disposed at least 180 degrees from one another.

In some embodiments, the suction bell comprises a main bell body defining the suction chamber, and a bell insert defining the pumping chamber, the main bell body and bell insert cooperating to form the tortuous air flow conduit.

In some cases, the internal suction bell wall extends generally horizontally across an upper extent of the suction chamber.

This aspect of the invention can, in some cases, advantageously inhibit the flow of expressed milk from the suction chamber, which is readily cleaned between uses, into the pumping chamber to contaminate pumping components.

In still further aspects of the invention, methods are provided for pumping breast milk. Such methods feature placing the breast receptacle of one of the above described breast pumps against a woman's breast and operating the breast pump to express milk from the breast.

The details of one or more embodiments are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION

Figure 1:
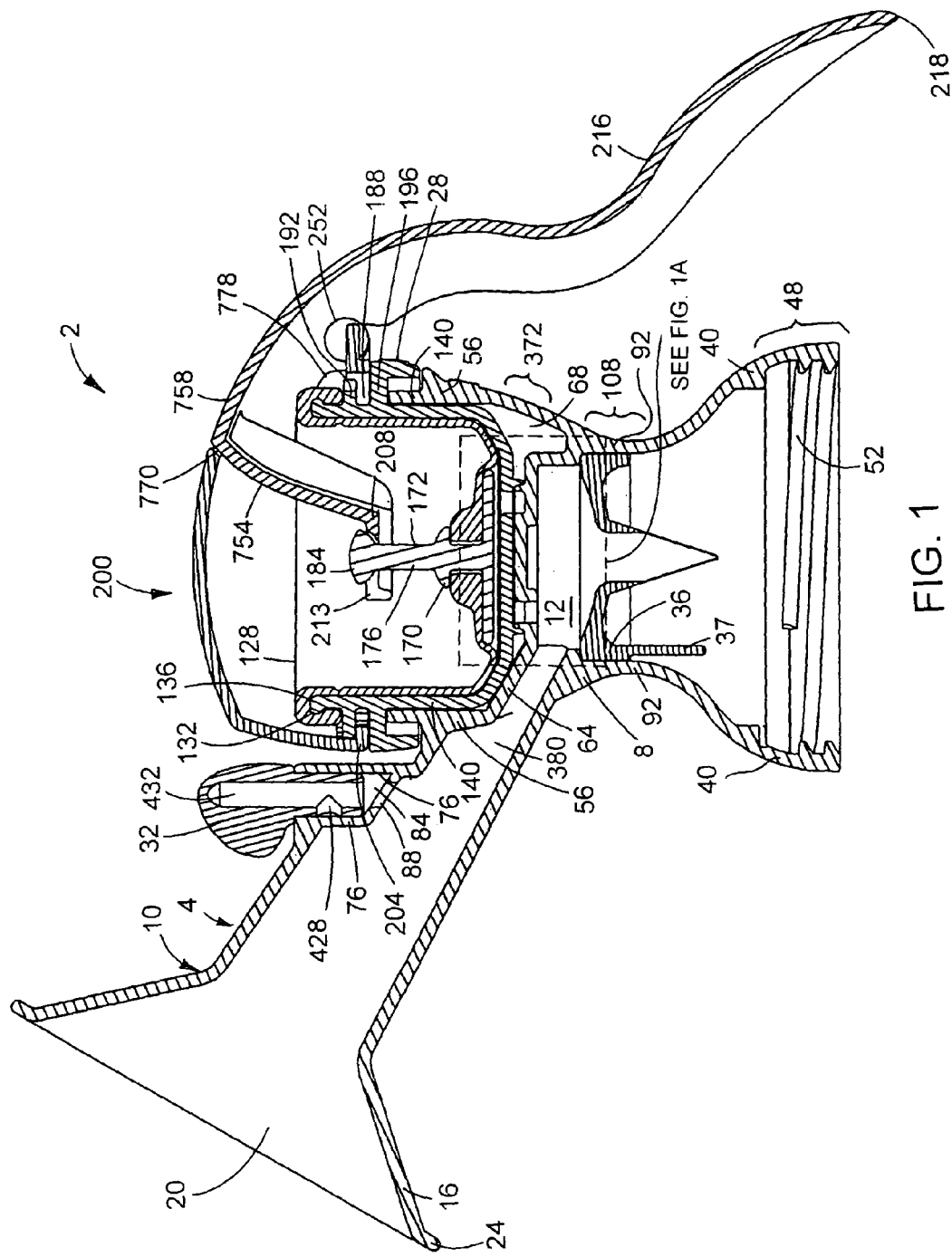
FIG. 1 is a cross-sectional view of a breast pump.
Figure 1A:
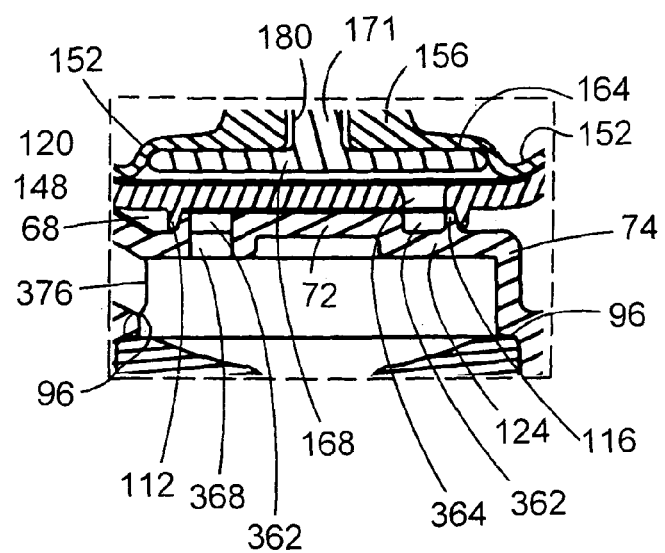
FIG. 1A is an enlarged view of area 1A of FIG. 1.

A cross-section of a breast pump 2 is shown in FIG. 1. Body 4 includes suction bell 8. Suction bell 8 defines suction chamber 12. Body 4 also includes breast shield 16, which interfaces with suction bell 8 at interface 10 such that breast shield 16 is in hydraulic communication with suction chamber 12. Breast shield 16 comprises breast receptacle 20 and a distal rim 24.

Suction bell 8 of body 4 also interfaces with pumping bell 28, valve 32 and valve 36. Wall 40 of body 4 define a bottle interface 48 that includes threads 52 to attach to a milk-storage bottle (not shown). Walls 56, 64, 72, 74 and 124 define a receptacle 68 within which pumping bell 28 is held against suction bell 8. Lip 112 extending from wall 120 of pumping bell 28 presses against a similar lip 116 of slightly smaller diameter extending from wall 124 of suction bell 8 to form a sealed interface and an outer margin of narrow annular conduit 362. Diaphragm 128 is secured at its top and peripheral edge portion 132 to top portion 136 of pumping bell 28, and partially defines, along with walls 120 and 140 of pumping bell 28, pumping chamber 148. Walls 152 and 156 of diaphragm 128 define receptacle 164 that holds platter 168 of plunger 172. Platter 168, flange 170, and extension 171 of plunger 172 abut wall 156 of diaphragm 128, with extension 171 extending through hole 180 of diaphragm 128. Extension 176 of plunger 172 features flared end 184, and wall 208 of pumping lever 216 defines receptacle 213 within which is seated flared end 184 is seated Walls 140, 192, and 196 of pumping bell 28 define a peripheral channel 188 for retaining certain tabs extending from cap/collar 200, including tab 204 (see the side of pumping bell 28 that is opposite pumping lever 216 in FIG. 1) enabling cap/collar 200 to rotate relative to pumping bell 28. Wall 76 defines a receptacle 84 for holding valve 32. Walls 92 and 96 define a receptacle 108 for holding valve 36, and tab 37 of valve 36 allows valve 36 to be easily removed from receptacle 108.

Figure 3:
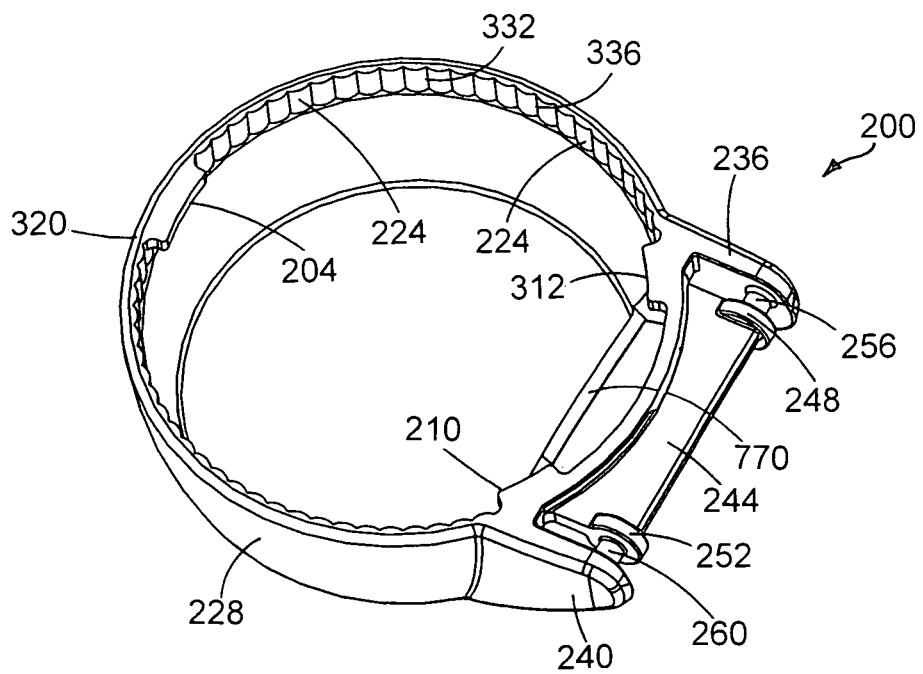
FIG. 3 is a perspective view of the cap/collar of the breast pump of FIG. 1.

Referring to FIGS. 1 and 3, pumping lever 216 attaches to and pivots around bars 256 and 260 of cap/collar 200, such that it can cyclically lift plunger 172 outward of suction bell 8, deflecting and deforming diaphragm 128 to expand pumping chamber 148, thus creating vacuum pressure within pumping chamber 148 and suction chamber 12 (provided, of course, that breast shield 16 is pressed against a woman's breast). Referring to the differently configured breast pump 608 of FIG. 20, diaphragm 716 is deflected and deformed outward of chamber 720. Referring to FIG. 1, a geometry which provides an initial volume of 82 cc for the combined volume of suction chamber 12, tortuous conduit 372, and pumping chamber 148, and a final volume (i.e., with diaphragm 128 deflected outward) of 99 cc, has been determined to induce acceptable rates of lactation. For this purpose, the suction chamber is regarded as beginning at interface 10 adjacent to breast shield 16.

Figure 2:
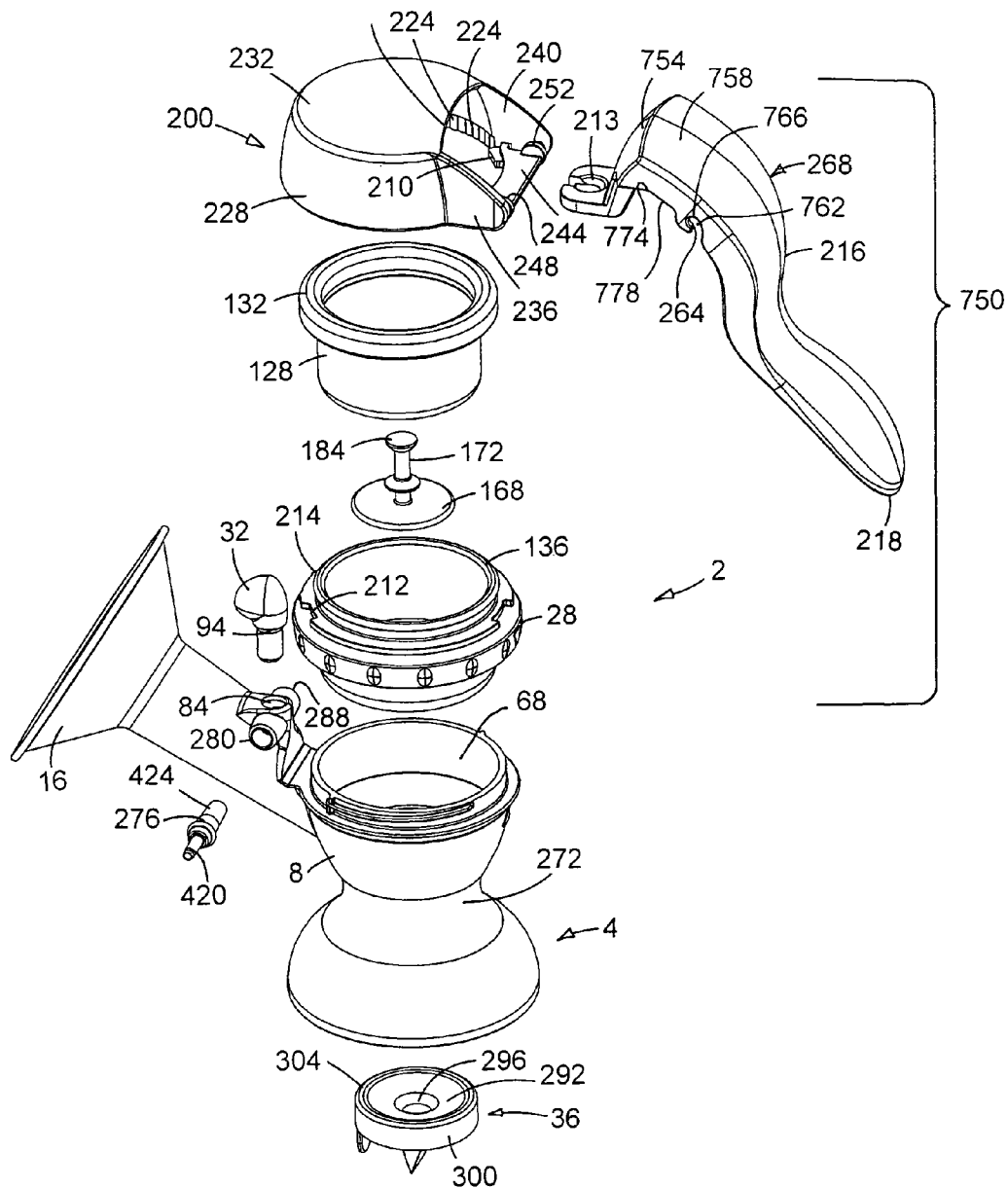
FIG. 2 is an exploded view of the breast pump of FIG. 1.
Figure 8:
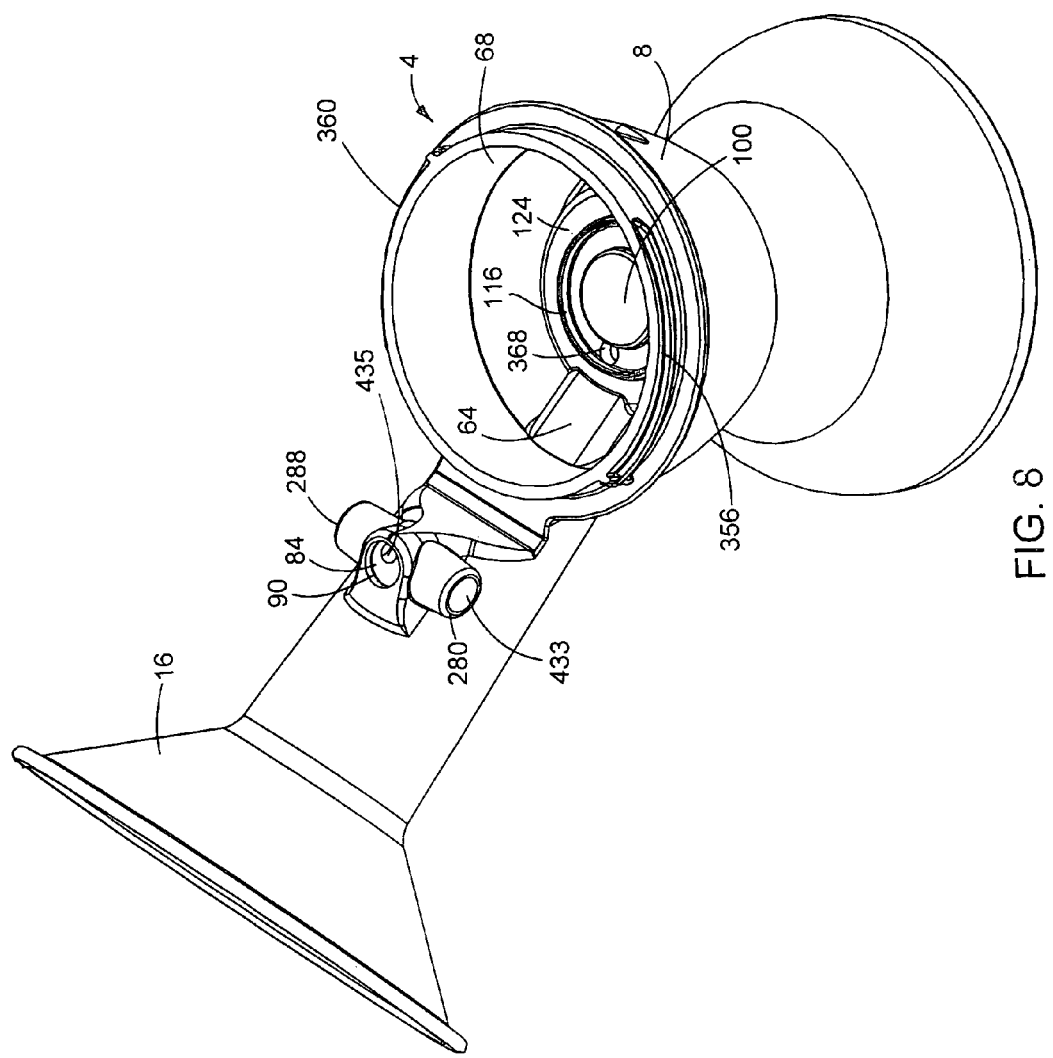
FIGS. 8 and 9 are upper and lower perspective views, respectively, of the body of the breast pump of FIG. 1.

Referring to FIGS. 1, 2 and 8, receptacle 84 positions conduit 432 of valve 32 adjacent to hole 88. Annular channel 90 within receptacle 84 accommodates an outward-facing annular protrusion 94 on the cylindrical side surface of valve 32, creating a seal between valve 32 and wall 76, locating and securely holding valve 32 within receptacle 84, and allowing valve 32 to rotate with respect to receptacle 84. Aperture 428 of conduit 432 can align either with conduit 433 of port 280, or conduit 435 of port 288, depending on which rotational position of valve 32 within receptacle 84 the user selects. In the illustrated embodiment, the conduit 432 defines a vertically oriented port that includes a longitudinal axis. The longitudinal axis of the vertically oriented port 432 is substantially parallel to the longitudinal axis of the milk-storage bottle or container.

Figure 4:
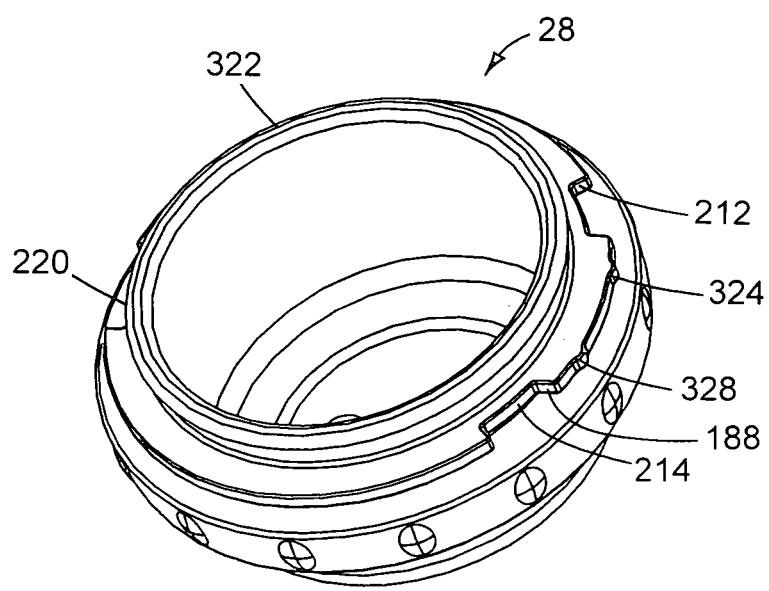
FIG. 4 is a perspective view of the pumping bell of the breast pump of FIG. 1.
Figure 9:
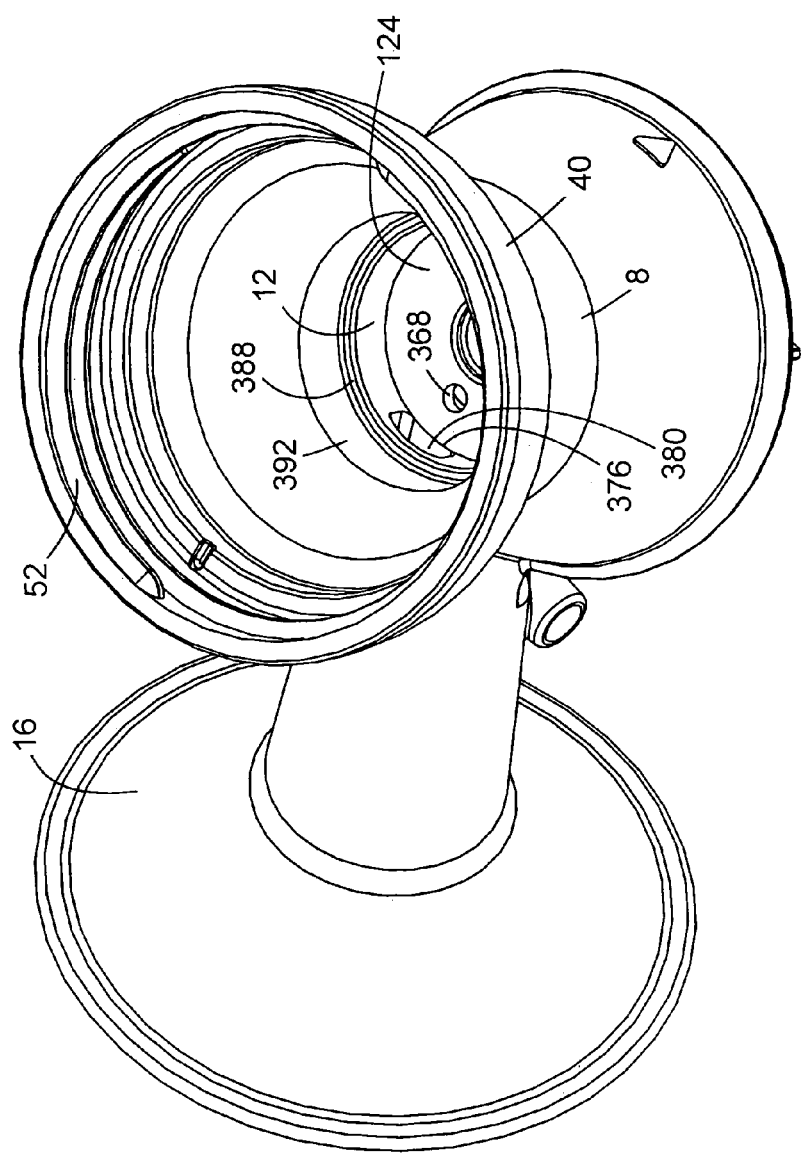
Figure 11:
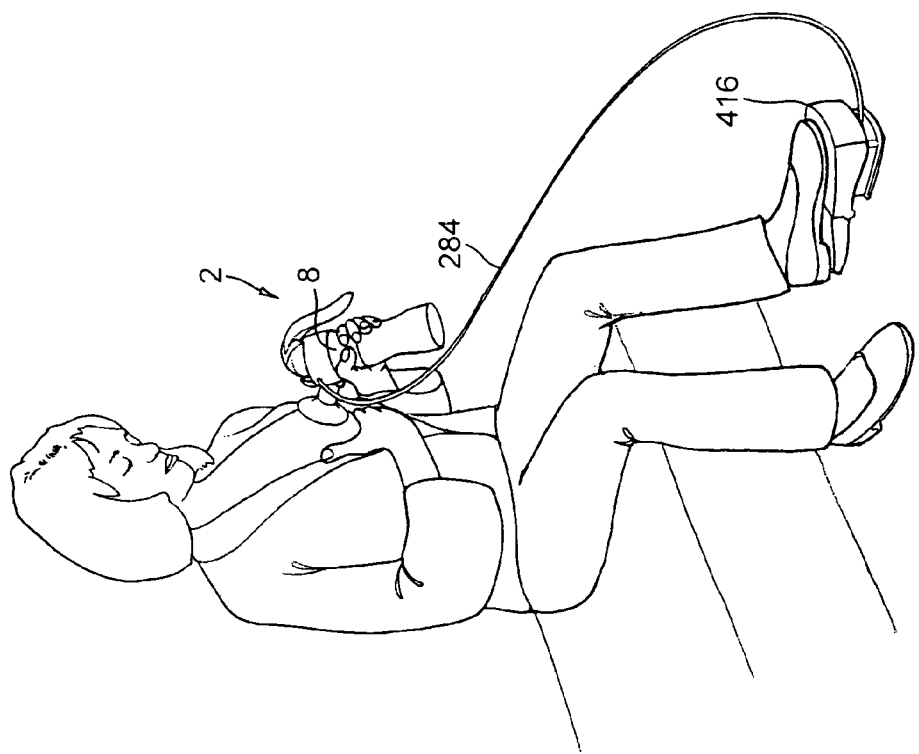
FIG. 11 illustrates foot operation of a breast pumping device to induce lactation.

FIG. 2 is an exploded view of breast pump 2. Receptacle 68 of suction bell 8, and pumping chamber 148 are visible. Referring to FIGS. 2, 3 and 4, installation of cap/collar 200 upon pumping bell 28 requires lowering tabs 204, 210 and 312 of cap/collar 200 through respective cutouts 220, 212 and 214 of pumping bell 28. Referring to FIGS. 2 and 3, protrusions 224 of cap/collar 200 share a common surface with, but are taller than, tabs 204, 208 and 312. Referring to FIGS. 2, 3 and 4, protrusions 224 participate in a detent which allows rotation of cap/collar 200 about pumping bell 28 to be at least temporarily arrested at the discretion of the user, causing pumping lever 216 to be secured in a pre-selected and pre-defined orientation with respect to breast shield 16, and allowing stable cyclical operation by the user. Referring to FIGS. 2 and 3, Collar wall 228, cap span 232, support arms 236 and 240, support shelf 244, and bosses 248 and 252 cooperate to hold bars 256 and 260 at an advantageous distance from pumping bell 28 for formation of a fulcrum for pumping lever 216, and provide a stiff scaffolding such that unwanted flexure is reduced, and smooth and well-controlled cyclical pumping action is possible. Again referring to FIGS. 2 and 3, bars 256 and 260 of cap/collar 200 pass through gaps 762 formed between hooks 264 and 268, and lodge in sockets 766 formed by the hooks. Referring to FIGS. 1 and 2, pumping lever 216 has a complex curved shape which both enables it to be gripped by the user with comfort during pumping, and allows it to conform to or nest against suction bell 8 where bell 8 defines a neck 272 around suction chamber 12. Pumping lever 652 of pump 608 of FIG. 20 also performs this nesting function. Referring to FIGS. 1, 2, and 11, tube fitting 276 can be inserted into port 280 of suction bell 8 so that an external pump 416 (shown in FIG. 11 as a foot-operable pump) can be employed by the user to cyclically draw a vacuum on suction chamber 12 through a flexible tube 284. Referring to FIGS. 1, 2 and 8, valve 32 inserts into receptacle 84 of suction bell 8, wherein it can optionally be oriented or turned so that port 280 or port 288 is activated, or so that neither port is activated (the orientation shown in FIGS. 1 and 2 corresponds to the latter). Ports 280 and 288 can face in opposite directions, and from the perspective of breast shield 16, they can fall on opposite sides of suction bell 8. Referring to FIGS. 2, 8 and 11, the fact that ports 280 and 288 fall on opposite side of suction bell 8 enables the user to connect flexible hose 284 to suction bell 8 on whichever side of suction bell 8 is convenient to the user. Referring to FIGS. 2 and 9, valve 36 has a shallow concave milk collection surface 292 with a drainage port 296 at its center. Surface 300 and flat top surface 304 of valve 36 are placed against respective mating surfaces 392 and 388 within suction bell 8 when valve 36 is installed.

Figure 5:
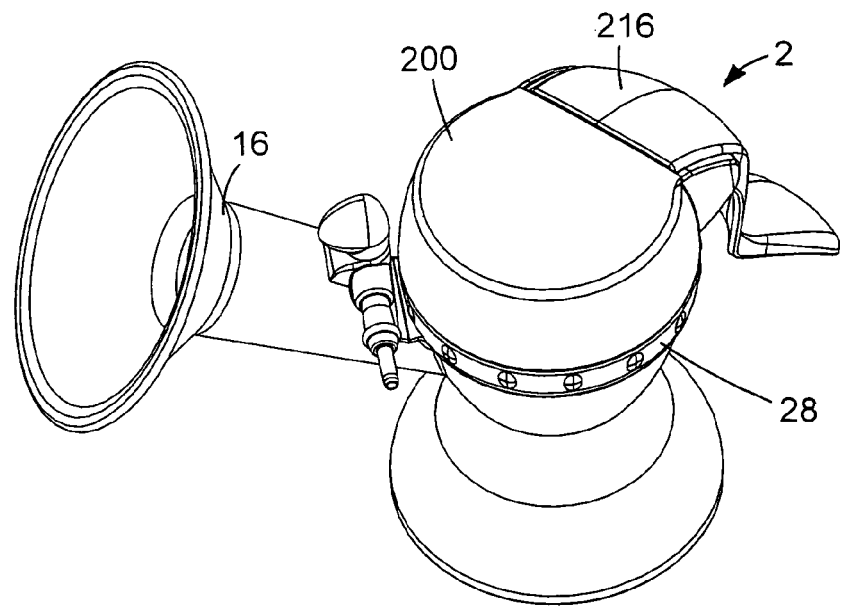
FIGS. 5 and 6 show the pumping lever rotated to two different positions.
Figure 6:
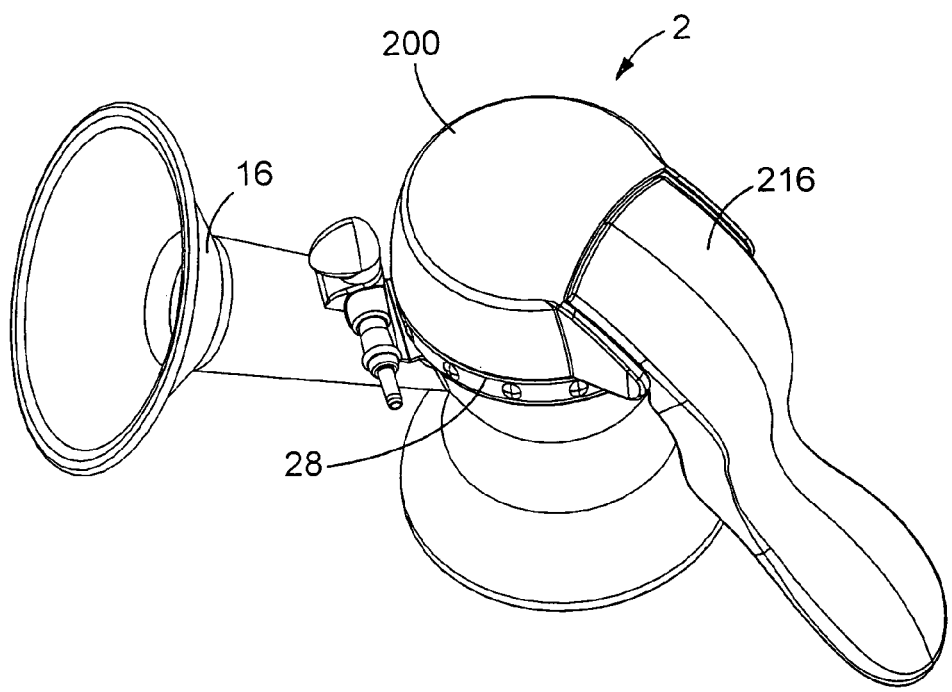

As shown in FIGS. 5 and 6, pump lever 216 can be made to assume multiple orientations with respect to breast shield 16 through the rotatable connection between cap/collar 200 and pumping bell 28. Referring to FIGS. 3 and 4, tabs 204, 210 and 312 are positioned around an inside perimeter at bottom side 320 of cap/collar 200 in such a way as to respectively match the positions of cutouts 220, 212 and 214 which are positioned around an outside perimeter near top side 322 of pumping bell 28. Such unevenly spaced matching patterns can be referred to as a "keying" arrangement, because it allows coupling between cap/collar 200 and pumping bell 28 only when they assume a single, specific rotational orientation with respect to each other.

Referring to FIGS. 1 and 2, to pump milk from her breast, a woman operating pump 2 must cyclically rotate pumping lever 216 about its fulcrum. The woman begins the cycle by first rotating pumping lever 216 so that end 218 of pumping lever 216 moves forward toward a retracted position for pumping lever 216 near suction bell 8. This causes plunger 172 to be raised outward of pumping bell 28, and diaphragm 128 to deform upward, creating a vacuum condition within pumping chamber 148 and suction chamber 12, and causing the woman's breast to lactate. The woman completes the cycle by quickly releasing pumping lever 216 and allowing pumping lever 216 to reassume its fully extended position as shown in FIG. 1. This allows a vacuum-decreasing return motion during which pressure forces and energy stored in deformed diaphragm 128 (and released when it relaxes) cause diaphragm 128 to pull downward on plunger 172, which in turn pulls downward on receptacle 213 of pumping lever 216, which causes end 218 of pumping lever 216 to move away from suction bell 8. Pressure within suction chamber 12 preferably returns to ambient at this point in the cycle, and pumped milk which has collected above surface 292 of valve 36 drains through port 296.

Figure 22:
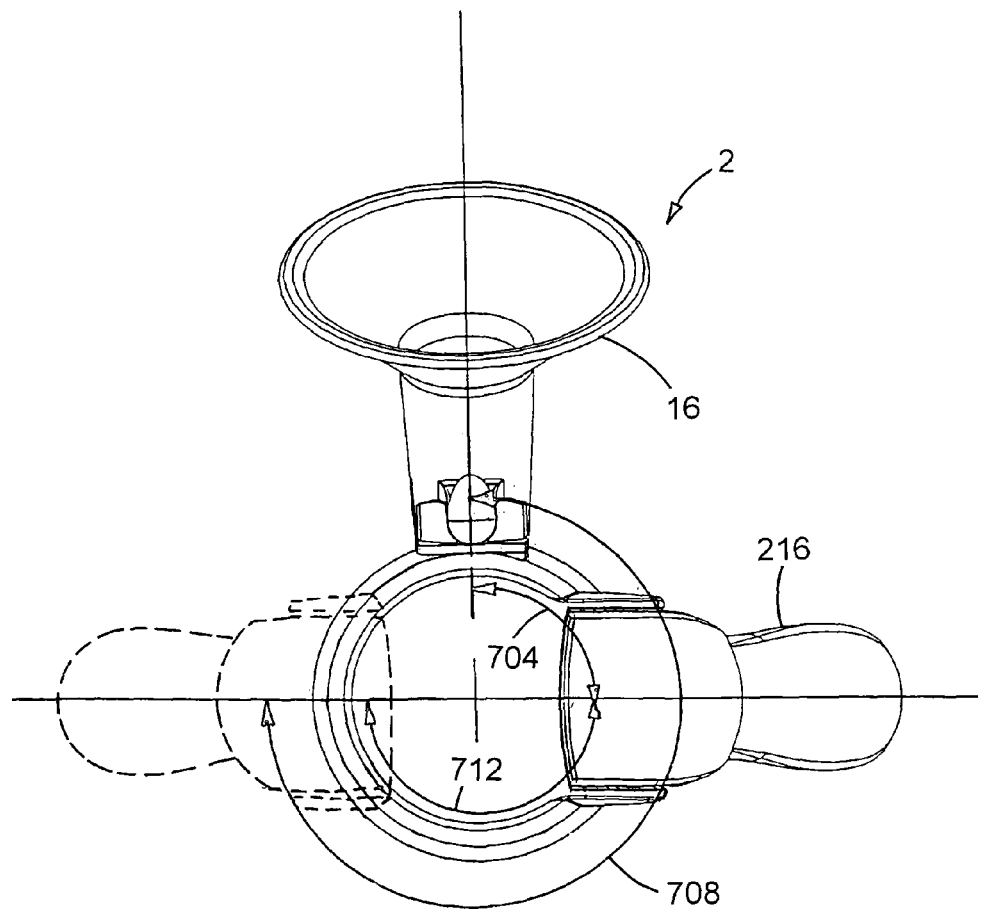
FIG. 22 is a top view of the breast pump of FIG. 1 illustrating two orientations of the pumping lever with respect to the breast shield.

Referring to FIGS. 1, 3, 4, 5, 6 and 22, protrusions 224 of cap/collar 200 cooperate with protrusions 324 and 328 of pumping chamber 28 to create detents that function to provide discrete orientations of pumping lever 216 with respect to breast shield 16, at each of which orientations pumping lever 216 can be cyclically rotated by the user to pump milk from her breasts. Specifically, when tabs 204, 210, and 312 of cap/collar 200 are lodged within channel 188 of pumping bell 28, protrusions 324 and 328 tend to settle into corresponding seams, e.g., seams 332 and 336, which seams are specifically peripherally spaced to correspond to the peripheral spacing of protrusions 324 and 328. Protrusions 324 and 328 lodge with relative firmness against the seams, and tend to remain lodged against the seams while the user operates pump 2. Five degrees of angular spacing between adjacent seams and twenty-five degrees of angular spacing between protrusions has been found to work well. Because many different pairs of seams can provide detent lodging for protrusions 324 and 328 in this way, many more than the two discrete orientations shown in FIGS. 5 and 6 can be achieved, at the convenience and option of the user. As shown in FIG. 22, pumping lever 216 can occupy a position having a rotational orientation with respect to breast shield 16 described by angle 704, which can measure, e.g., as low as 45 degrees. Another position for pumping lever 216 is shown, which has a rotational orientation with respect to breast shield 16 described by angle 708, which can measure, e.g., as high as 315 degrees. This provides a range of adjustment described by angle 712, which can measure, e.g., as high as 270 degrees, and which enables many discrete angular orientations within that range that a given user, who may be left handed or right handed, can select based on what will provide the most comfort during manual operation of pump 2. Of course, a given user may wish slightly different angular orientations at different times when pumping her left or right breast with the same hand, and pump 2 as shown can allow for that. As well, a user may choose to switch hands, either once or repeatedly, during pumping operation, which pump 2 can also allow.

Figure 7:
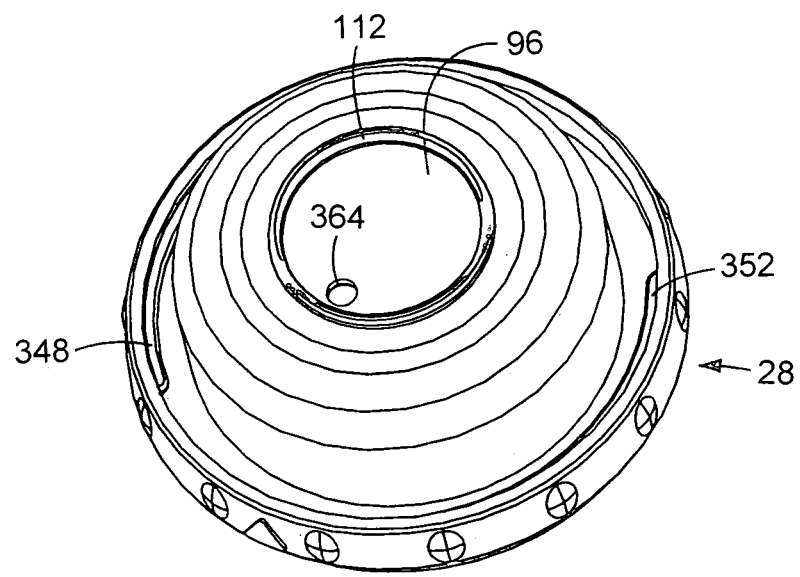
FIG. 7 is a perspective view of the pumping bell of the breast pump of FIG. 1.

Referring to FIGS. 7 and 8, pumping bell 28 and suction bell 8 attach one to the other by a quarter-turn fastening arrangement. Quarter turn fastener threads 352 and 348 of pumping bell 28 respectively press and slide against corresponding threads 356 and 360 of suction bell 8, holding pumping bell 28 securely in place. Referring to FIGS. 1, 2, 7, 8, and 9, portions of pumping bell 28 and suction bell 8 combine to create a narrow and tortuous conduit 372 that hydraulically connects pumping chamber 148 with suction chamber 12. When pumping bell 28 is seated within receptacle 68 of suction bell 8 in pump 2, and the two components are secured together by the quarter-turn fastening arrangement, the force of the quarter turn fastening arrangement is absorbed by lips 112 and 116, which press together as a result to form the seal at the outer margin of narrow annular conduit 362, of which the side surfaces of wall 72 forms the interior margin. Referring to FIGS. 1, 7 and 8 specifically, when pumping bell 28 is secured to suction bell 8, surfaces 96 and 100 are brought in close spaced relation. Besides completing the narrow annular conduit 362, this arrangement minimizes the total volume of air between the two chambers, and substantially restricts air flow between the two chambers to narrow annular conduit 362. It is not necessary for surfaces 96 and 100 to touch, and it is preferable that they do not, since that would tend to subtract from the compressive force acting to seal lips 112 and 116 together. A hydraulic connection between pumping chamber 148 and narrow annular conduit 362 is created by perforation 364 in wall 120 of pumping bell 28. Also, a hydraulic connection between suction chamber 12 and narrow annular conduit 362 is created by perforation 368 in wall 124 of suction bell 8, which in the assembly can be 180 degrees offset from (i.e., on the opposite side of narrow annular conduit 362 from) perforation 364 in pumping bell 28. Perforations 364 and 368 can also be oriented normal to the curved planar path of narrow annular conduit 362.

Offset perforations 364 and 368, together with narrow annular conduit 362, define narrow tortuous conduit 372 which hydraulically connects pumping chamber 148 of pumping bell 28 with suction chamber 12 of suction bell 8, so that during pumping operation of pump 2, the pressure within the two chambers will tend to be the same. At the same time, however, pumping chamber 148 and suction chamber 12 are physically separated. Also, perforation 368 at one end of narrow tortuous conduit 372 is positioned away from the flow of pumped milk within suction chamber 12 during normal pumping operation. As well, narrow tortuous conduit 372 includes multiple changes in conduit direction. These factors all contribute to the desired result that the milk flowing through suction chamber 12 during normal pumping operation of pump 2 will be prevented from entering pumping bell 28 through perforation 364 via tortuous conduit 372. This prevents pumping chamber 148 from being contaminated with pumped milk during normal pumping operation of pump 2. And because pumping bell 28, along with cap/collar 200, diaphragm 128, and pumping lever 216, can be easily detached from suction bell 8 by releasing quarter-turn fastener threads 348, 352, 356 and 360, those parts need not be cleaned and sanitized between uses by means of the same rigorous process as will those components of pump 2 below pumping bell 28 which will normally be in contact with pumped milk (e.g., suction bell 8, breast shield 16 of body 4, and valve 36).

One particularly advantageous feature of pump 2 of FIGS. 1 and 2 is that the number of parts that must be rigorously cleaned between pumping sessions is relatively small compared to the total number of parts that make up the pump. Parts which come in contact with breast milk during normal operation, and should therefore generally be rigorously sanitized between pumping sessions, include body 4 and valve 36. Preferably, such sanitation includes using tab 37 of valve 36 to remove valve 36 from body 4, and then cleaning and sanitizing the parts in the disassembled state. All other parts should also be disassembled from body 4 before the latter is cleaned and sanitized. For example, the user will urge valve 32 outward of receptacle 84 until annular protrusion 94 snaps out of annular channel 90, allowing valve 32 to detach. Valve 32 can be washed using a combination of water and ordinary dish detergent, rinsed with fresh water, and allowed to dry. The user will also twist pumping bell 28 with respect to body 4, thus releasing the force of the quarter-turn fastener and allowing pumping bell 28 to lift off body 4. At this point the remaining parts of pump 2 will also have been detached from body 4, because the fastening arrangements between all of those parts and body 4 necessarily include the quarter-turn fastening arrangement between pumping bell 28 and body 4. Referring to FIG. 1, Pumping bell 28, diaphragm 128, plunger 172, cap/collar 200 and pumping lever 216 comprise subassembly 750, which, because not contacted by the flow of breast milk during normal use of pump 2, need not be disassembled in preparation for rigorous sanitation of individual parts, and instead should only be subjected, fully assembled, to light cleaning followed by a fresh water rinse and air drying between pumping sessions, as described above with regard to valve 32.

Another aspect of the design of subassembly 750 prevents even its partial disassembly when suction bell 28 is attached via the quarter-turn fastening arrangement to body 4. Another aspect of the design of subassembly 750 discourages disassembly of subassembly 750 in general, even when it has been detached from body 4. For understanding these features, and their advantages, it will be helpful to consider how components of subassembly 750 are assembled.

For assembly of subassembly 750, flared end 184 of plunger 172 is urged toward receptacle 164 of diaphragm 128, and is inserted through hole 180. Extension 176 and flange 170 follow flared end 184 through hole 180 to permit wall 156 of diaphragm 128 to lodge in the space between flange 170 and platter 168 of plunger 172. Diaphragm 128 is then lowered with plunger 172 past rim 136 of pumping bell 28, and edge region 132 of diaphragm 128 is pushed onto rim 136, forming an air-tight seal. Separately, pumping lever 216 is oriented so that receptacle 213 points downward, and receptacle 213 is then inserted downward at a relatively steep angle through the gap between walls 236 and 240 of cap/collar 200. Insertion continues until the entirety of curved surface 754 of pumping lever 216 has entered the gap, along with a portion of curved surface 758. Once latching hooks 264 and 268 have been lowered below the level of bars 256 and 260, pumping lever 216 is urged sideways toward support shelf 244 so that bars 256 and 260 are directly above corresponding gaps 762 formed between the ends of respective hooks 264 and 268 and the rest of pumping lever 216. Cap/collar 200 is then urged downward toward pumping lever 216 so that bars 256 and 260 pass through corresponding gaps 762 and into sockets 766 formed by respective hooks 264 and 268, at which time a moderate amount of additional force is needed to move bars 256 and 260 past an interference between the parts, and to allow bars 256 and 260 to securely and rotatably seat within sockets 766. Free rotation of pumping lever 216 around bars 256 and 260 is then possible, and the combined geometry of pumping lever 216 and cap/collar 200 causes curved surface 754, during this rotation, to remain close to edge 770 of wall 232 of cap/collar 200 during angular translation (i.e., the radius which roughly describes curved surface 754 originates approximately at a line coaxial with bars 256 and 260).

The final stage in the assembly of subassembly 750 includes forming the separate connections between receptacle 213 of pumping lever 216 and plunger 172 on the one hand, and between cap/collar 200 and pumping bell 28 on the other. First, flared end 184 of plunger 172 is seated in receptacle 213 of pumping lever 216. To do this, pumping lever 216, which will by now be attached to cap/collar 200 in the manner described above, should be temporarily rotated beyond the fully extended position (e.g., as shown in FIG. 1) so that end 218 is rotated even farther to the right than is shown in FIG. 1. This is an "over-rotated" condition of pumping lever 216 with respect to cap/collar 200, and it results in receptacle 213 of pumping lever 216 extending well below lower surface 320 of cap/collar 200. Receptacle 213 is caused to hook under flared end 184 of plunger 172. Flared end 184 is then pulled temporarily upward (pulling diaphragm 128 with it) to meet receptacle 213 to avoid interference among components. Once the hooking step is complete, cap/collar 200 is rotated as necessary to ensure that tabs 204, 210 and 312 are respectively aligned with cutouts 220, 212 and 214. And once keying alignment is achieved, the tabs are lowered so that they lodge in channel 188. Pumping lever 216 will automatically assume the fully extended position as shown in FIG. 1, in part because diaphragm 128 tends to move toward the shape shown in FIG. 1, and in part because it is restricted from rotating further by mechanical interference as explained below. Cap/collar 200 is then rotated away from the keying alignment orientation with pumping bell 28, and into an orientation in which seams between protrusions 224 of cap/collar 200 cooperate with protrusions 324 and 328 of pumping bell to hold cap/collar 200, along with pumping lever 216, in a distinct and stable rotational orientation with respect to pumping bell 28.

Subassembly 750 is now complete, and pumping lever 216 can no longer "over-rotate" in the way it did prior to assembly of cap/collar 200 atop pumping bell 28 (i.e., receptacle 213 cannot dip any further into pumping bell 28 than is shown, e.g., in FIG. 1). This is because edges 774 (one on either side of pumping lever 216) are blocked by edge region 132 of diaphragm 128, as they are supported by rim 136 of pumping chamber 128. Edges 778 of pumping lever 216 are similarly blocked. Beneficially, this makes it physically impossible to remove pumping lever 216 from its rotational connection on bars 256 and 260 without disassembling cap/collar 200 from pumping bell 28. The significance of this latter feature will be apparent when considered in light of the following. Attachment of subassembly 750 to body 4 must take place at the quarter-turn fastening arrangement between pumping bell 28 and suction bell 8. Once this connection is made, it will be impossible to rotate cap/collar 200 to the orientation in which the tabs of cap/collar 200 are keyed to the cutouts of pumping bell 28. The reason for this is that mechanical interference between pumping lever 216 and breast shield 16 (made inevitable because over-rotation of pumping lever 216 is prevented) subtracts upwards of 90 degrees from what would otherwise be a complete circle of rotation by cap/collar 200 with respect to pumping bell 28. And the orientation which allows cap/collar 200 to lift off pumping bell 28 (i.e., the keying or matching orientation between the tabs of cap/collar 200 and the cutouts of pumping bell 28) falls, by design, approximately in the middle of this 90 degree span of rotation. Thus the user must remove subassembly 750 from body 4 before being able to disassemble any portion of subassembly 750. This means that subassembly 750 must be removed intact if it is to be removed at all. This feature of pump 2, combined with the fact that disassembly of subassembly 750 requires a specific order of combined manipulation, advantageously discourages unnecessary disassembly of subassembly 750.

Referring to FIGS. 1, 8 and 9, during pumping operation, unoccupied portions of receptacle 68 are outside the combined volume of the pumping chamber 148, narrow tortuous conduit 372, and suction chamber 12. As such, those portions will not be subjected to pressure cycling during pumping.

Referring to FIGS. 1 and 9, valve interface portion 108 of suction bell 8 is shown, as well as a portion of suction chamber 12, perforation 368, opening 376 to channel 380 which leads to breast shield 16, and wall 40 of body 4 which flares out and forms internal threads 52 which secure to mating external threads of a milk storage bottle (not shown). Referring to FIGS. 2 and 9, in assembled pump 2 and during operation, top surface 304 and surface 300 of valve 36 respectively abut bottom surface 388 and surface 392 of suction bell 8. Friction between valve 36 and suction bell 8 at their respective surfaces 300 and 392 helps keep valve 36 seated against suction bell 8, where valve 36 forms part of suction chamber 12.

Figure 10:
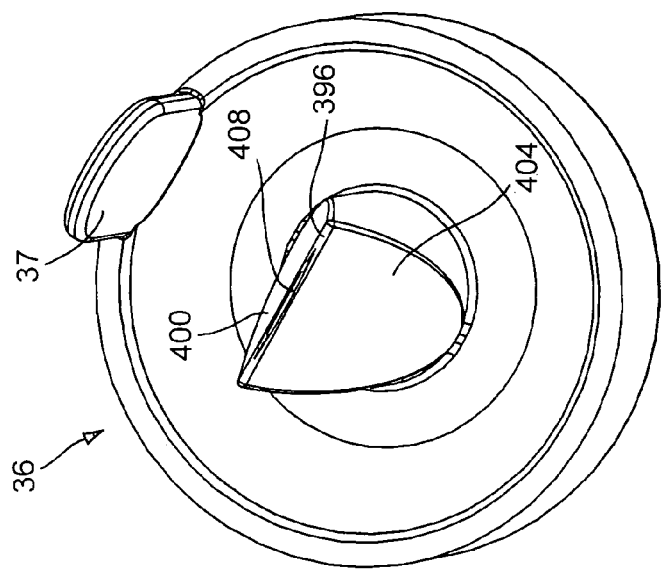
FIG. 10 is a perspective view of a valve of the breast pump of FIG. 1.

Referring to FIGS. 2 and 10, drainage port 296 of valve 36 leads to a duckbill portion 396. The two bills 400, 404 of duckbill portion 396 tend to seal against each other when suction chamber 12 is subjected to vacuum pressure during pumping operation, and conversely tend to relax and to reveal opening 408 when vacuum pressure is relieved, either between cycles of vacuum pressure or when the pumping has ceased, allowing pumped milk to drain from drainage port 296 through opening 408 under the force of its own weight. Tab 37 facilitates insertion and removal of valve 36 from valve interface portion 108 of suction bell 8.

Figure 12:
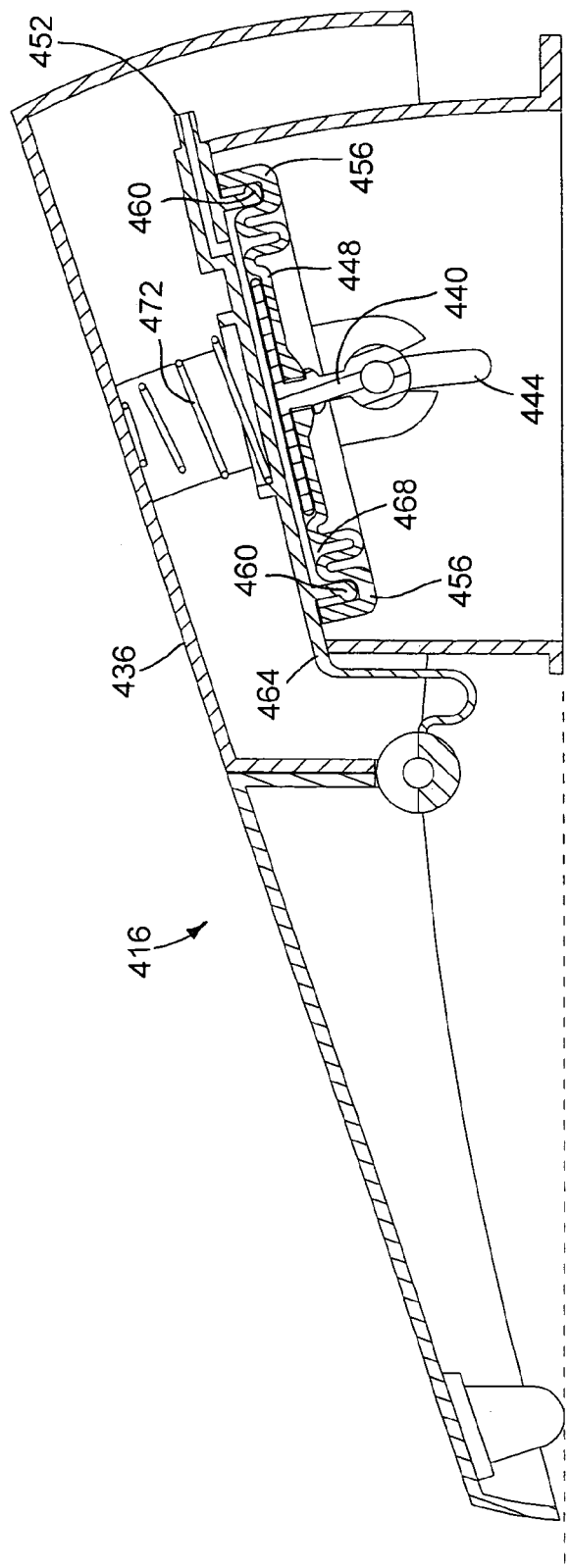
FIG. 12 is a cross-sectional view of the foot pump of the breast pumping device of FIG. 11.
Figure 14:
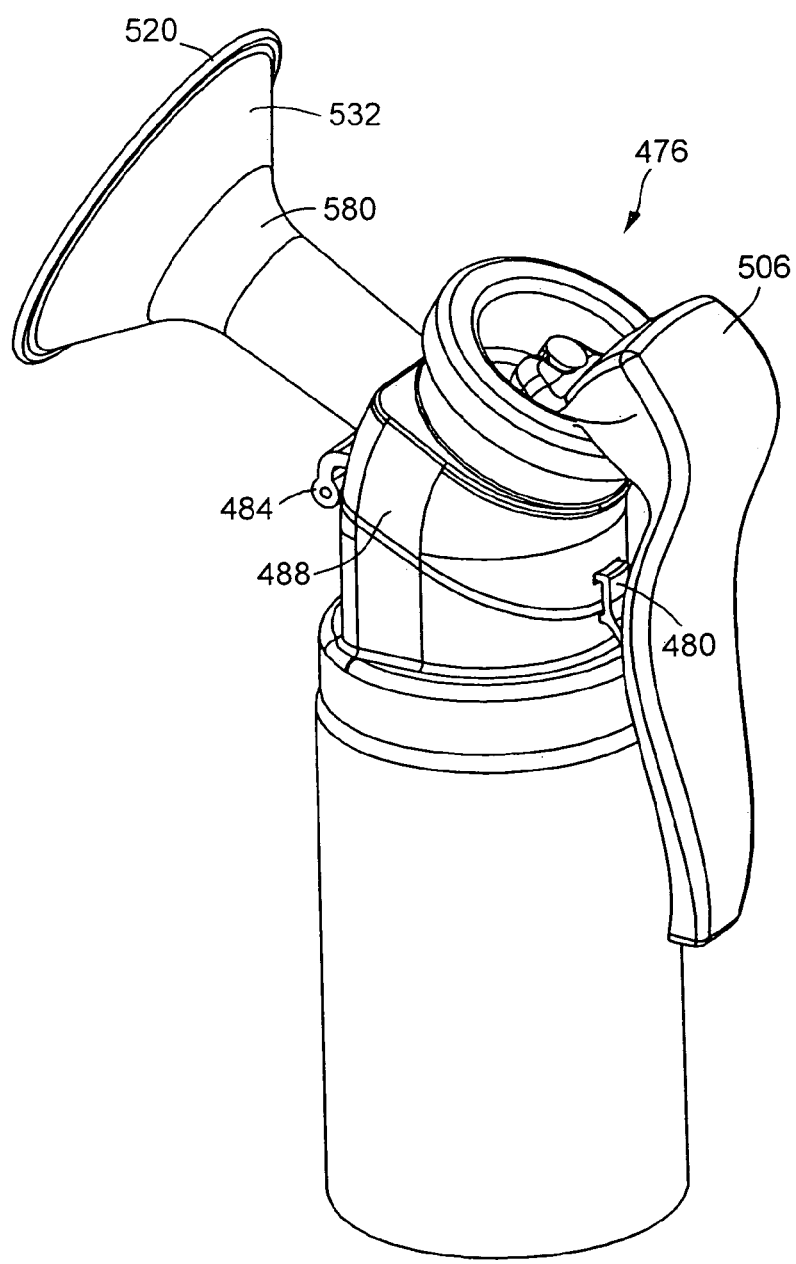
FIG. 14 is a perspective view of another breast pump.

Referring to FIGS. 2, 11 and 12, a woman utilizes breast pump 2 in an external pumping mode, in which a flexible tube 284 is mechanically attached to suction bell 8 such that foot-operated pump 416 is placed in hydraulic communication with suction chamber 12 (not shown), the woman's breast is inserted into breast shield 16, and the woman uses her foot to cyclically operate foot pump 416, which provides the cycling vacuum pressure needed to pump milk from her breast. In such an arrangement, flexible tube 284 can be attached to end 420 of fitting 276, end 424 of fitting 276 can be inserted into, e.g., port 280 of suction bell 8, valve 32 can be turned so that aperture 428 of conduit 432 is oriented in the direction of port 280 so as to activate the port, and foot pump 416 of FIG. 12 can be used to create cycling vacuum pressure. Referring to FIG. 12, plate 436 can be depressed, pushing plunger extension 440 downward along track 444, which in turn deflects diaphragm 448 downward. Because edge 456 of diaphragm 448 is sealed around lip 460 of fixed plate 464, the deflection of diaphragm 448 creates suction at port 452 of foot pump 416. After the user releases the load on plate 436, spring 472 returns plate 436 to its extreme upward position, as shown in FIG. 12.

Figure 13:
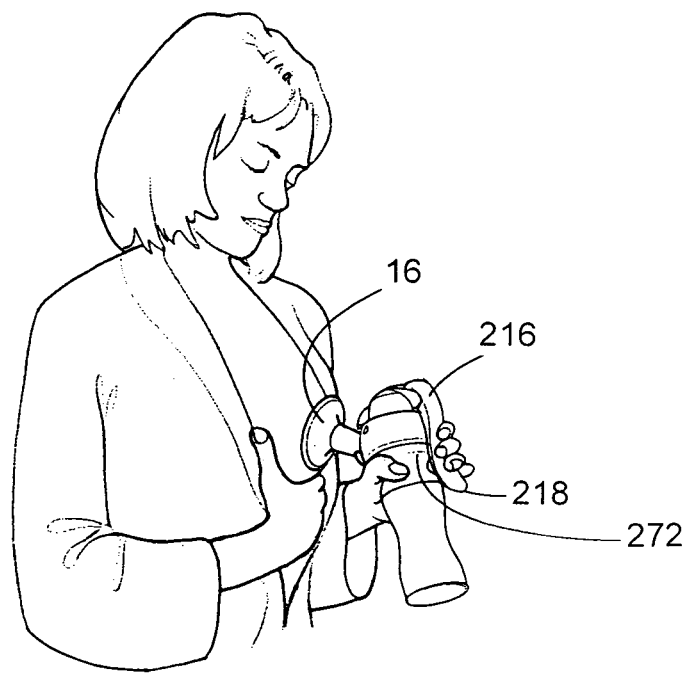
FIG. 13 illustrates manual operation of a breast pumping device to induce lactation.

Referring to FIGS. 1, 2, and 13, a woman can utilize breast pump 2 in a manual pumping mode. Valve 32 is turned so that neither port 280 nor port 288 is activated (see FIGS. 1 and 2), capping off or closing hole 88 in suction chamber 12, and the woman uses her left hand to cyclically deflect pumping lever 216 (and end 218 with it) by turns toward and away from suction bell 8, creating a cyclical vacuum inside the pumping and suction chambers 148, 12. The woman may adjust the orientation of pumping lever 216 with respect to breast shield 16 to achieve the most comfortable angle at which to grip and deflect pumping lever 216 toward suction bell 8.

Body 4 can comprise polycarbonate, for transparency and strength. Pumping bell 28 and fitting 276 can comprise ABS (acrilonitrile butadiene styrene). The following parts can comprise polypropylene: pumping lever 216, cap/collar 200, valve 32, plunger 172. Diaphragm 128 can comprise TPE (thermoplastic elastomer) and valve 36 can comprise silicone.

Figure 21:
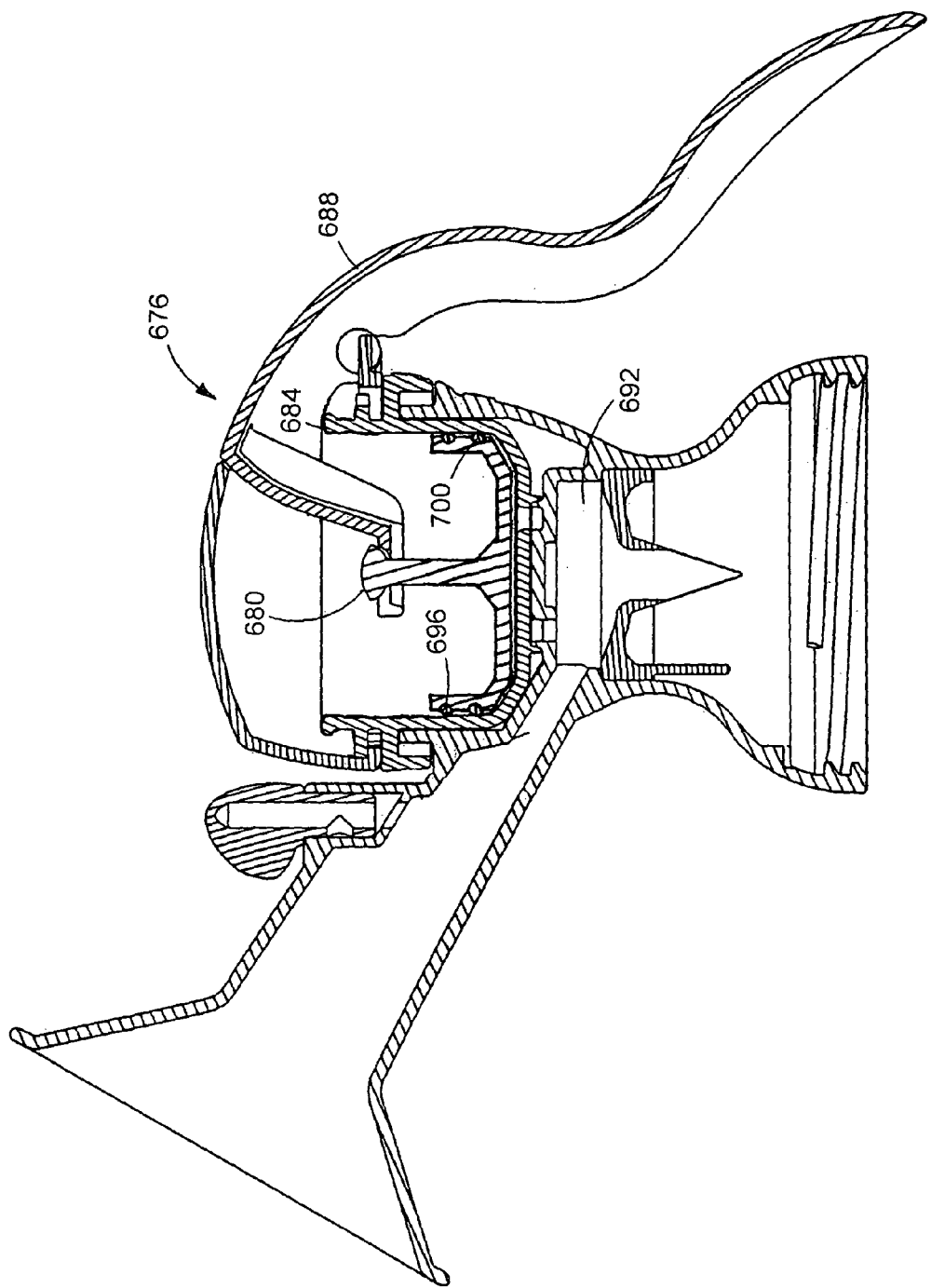
FIG. 21 is a cross-sectional view of a breast pump with a sliding pump plunger.

Referring to FIG. 21 breast pump 676 is shown, similar in many respects to pump 2 of FIGS. 1 and 2, but lacking parts corresponding to plunger 172 and diaphragm 128 of pump 2. Piston 680 of breast pump 676 is retractably disposed within cylinder 692 of pumping bell 684 for cyclical movement within chamber 684. Piston 680, in cooperation with the pumping lever 688, can provide a cyclical vacuum within cylinder 692. Flexible seals 696 and 700 can be placed between piston 680 and the surface of pumping chamber 684 to provide substantially airtight sliding operation for efficient pumping.

Figure 15:
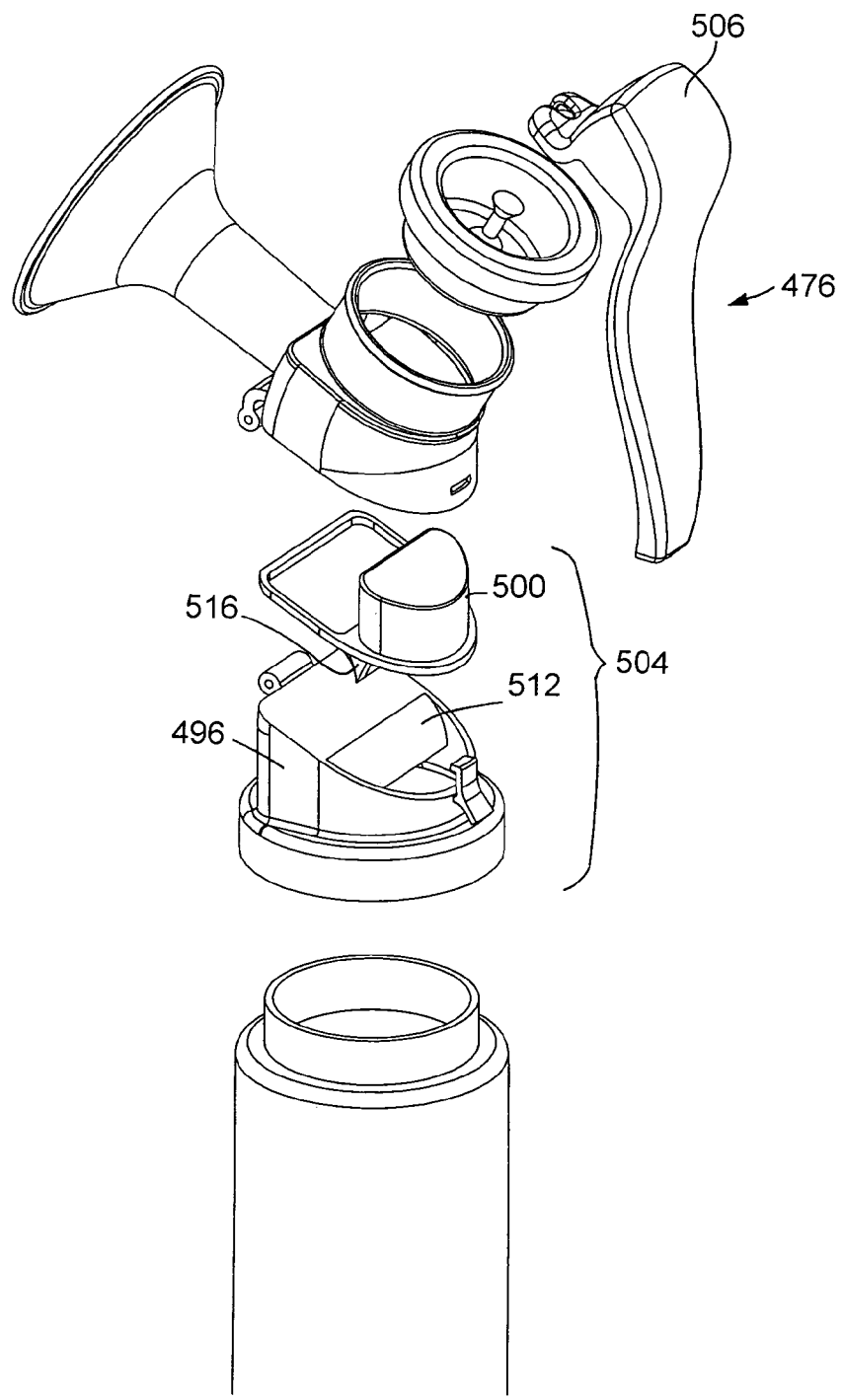
FIG. 15 is an exploded view of the breast pump of FIG. 14.
Figure 16:
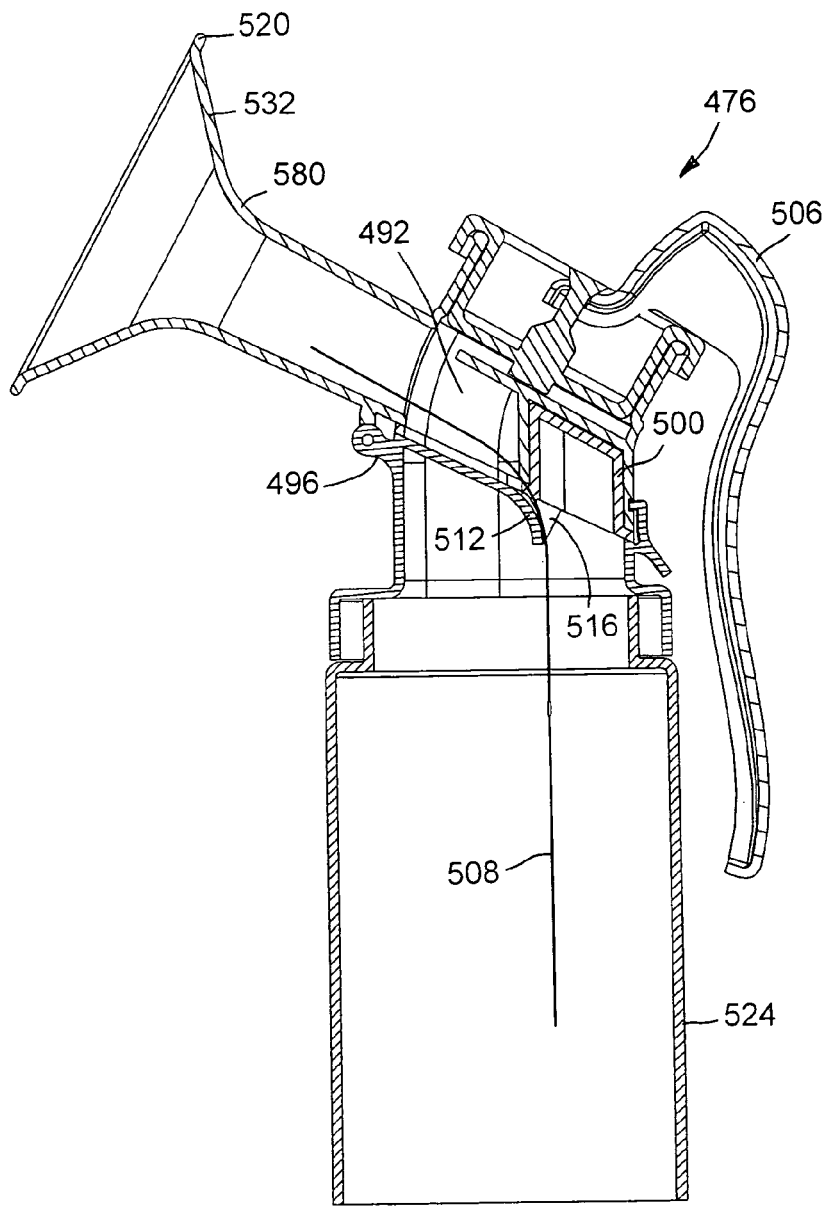
FIG. 16 is a vertical cross-sectional view of the breast pump of FIG. 14, showing an internal liner.

Referring to FIGS. 14-17, manual breast pump 476 is shown. Pump 476 lacks a valve and ports to permit external pumping, but is similar in certain other ways to pump 2 of FIGS. 1 and 2. Pump 476 includes a latch 480 and a hinge 484, which together permit suction bell 488 to be opened and suction chamber 492 to be exposed, and also permit suction bell 488 to be closed and secured. Referring to FIG. 15, pump 476 is shown in an exploded assembly view. Rigid member 496 and flexible member 500 combine to form portions of valve 504. FIG. 16 shows a cross-section of the assembly of pump 476, with a plastic liner 508, comprising a flexible conduit for conducting pumped breast milk positioned inside pump 476. Liner 508 passes through valve 504 between a downward sloping wall 512 of rigid member 496 and a downward sloping wall 516 of flexible member 500. When the user, by cyclically operating pumping lever 506, subjects suction chamber 492 to vacuum pressure as compared to the ambient pressure, downward sloping wall 516 of flexible member 500 will tend to seal against downward sloping wall 512 of rigid member 496, preventing inward flow from outside pumping chamber 492, either of pumped milk through the conduit formed by liner 508, or of air around liner 508. With liner 508 in place, suction bell 488 of pump 476 may not need to be as rigorously sanitized between uses, as milk-conducting liner 508 prevents it from coming in contact with pumped milk. Similarly, all other parts of pump 476 which liner 508 shields from the flow of milk may not need to be as rigorously sanitized, and liner 508 can extend to and beyond rim 520 of breast shield 532, as described below.

Figure 17:
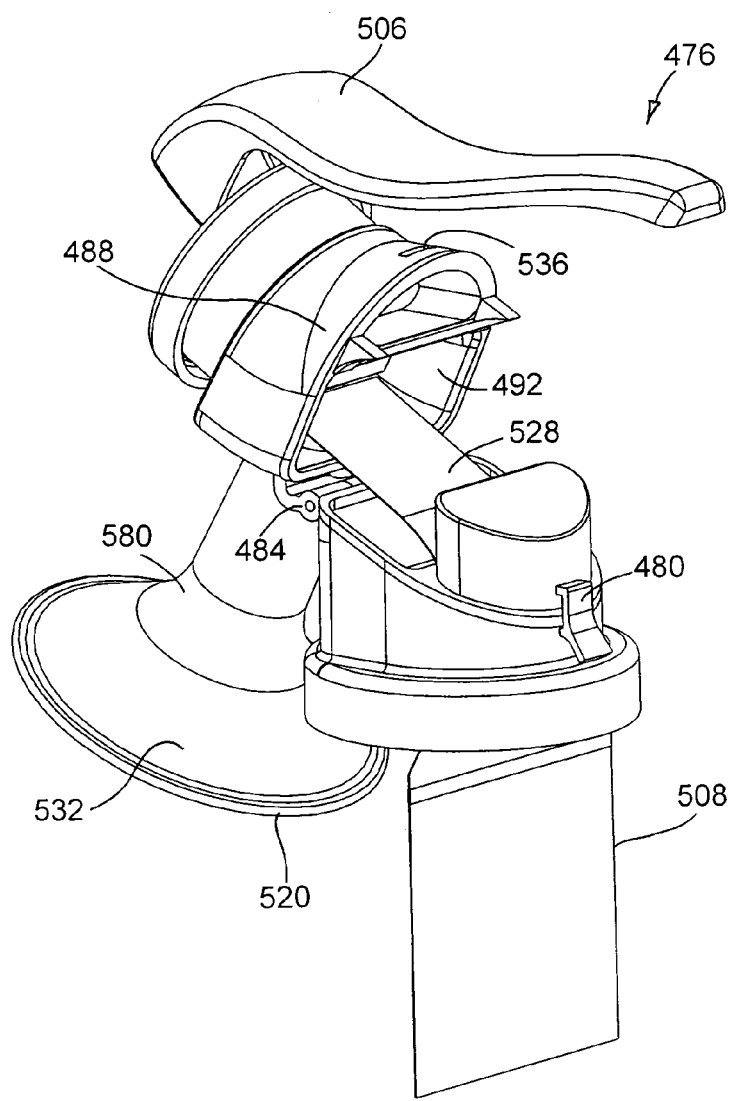
FIG. 17 shows the breast pump of FIG. 14, with the suction bell hinged open to expose the suction chamber and liner inside.

Referring to FIG. 17, pump 476 is shown (without a milk collection bottle 524). Latch 480 is loose, and hinge 484 is flexed to reveal suction chamber 492. Narrow conduit portion 528 of liner 508 passes through suction chamber 492. This hinging function allows the user to easily thread liner 508, for example from below valve 504, up through valve 504, into suction chamber 492, and from there into the channel (not shown) leading to breast shield 532. After the threading of liner 508 is complete, the user can rotate hinge 484, and secure latch 480 into hole 536 of suction bell 488.

Figure 18:
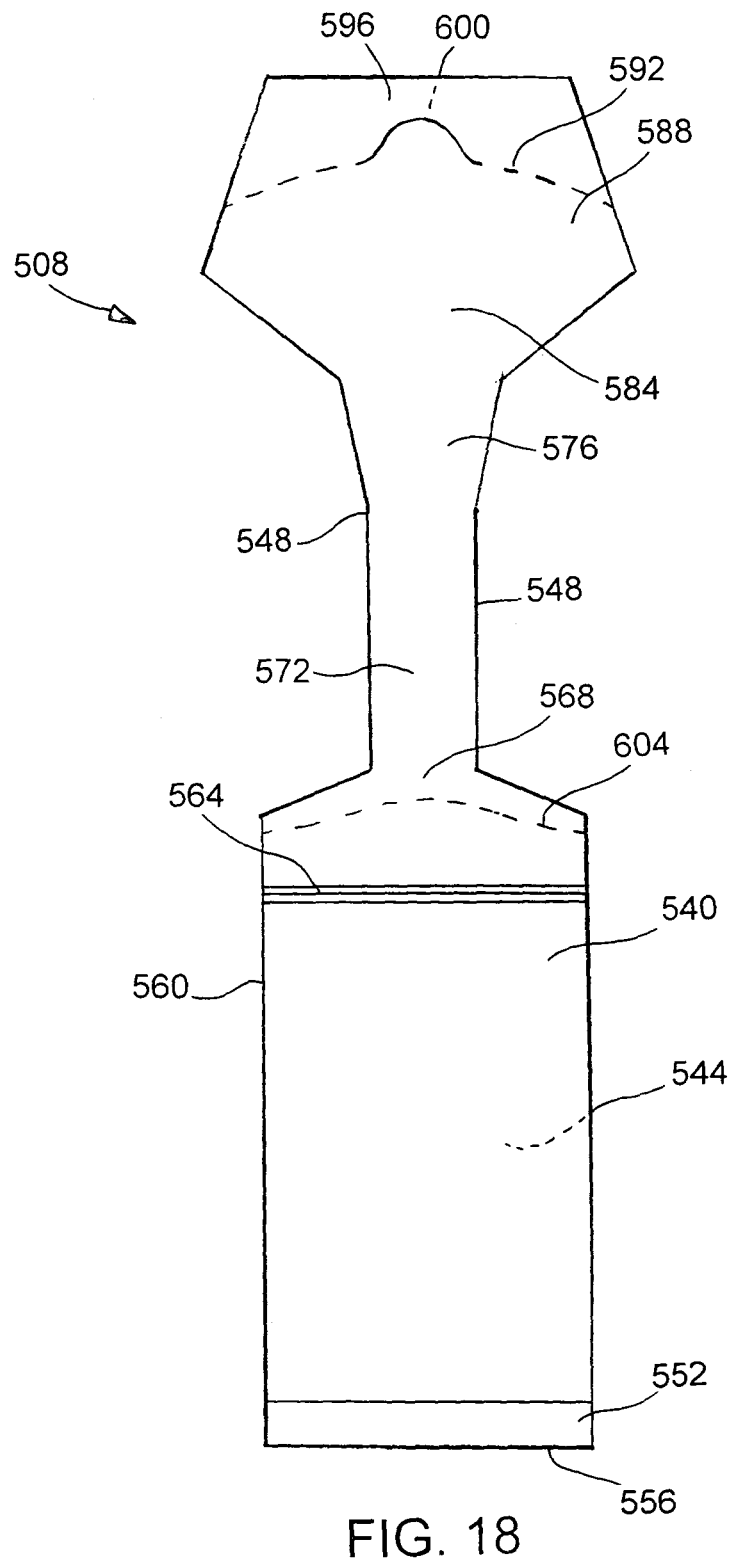
FIG. 18 is a face view of a breast pump liner.

Referring to FIGS. 16 and 18, an optional configuration of liner 508 is shown. Two thin flexible plastic sheets 540 and 544, preferably comprising low-density polyethylene (LDPE), and optionally comprising linear-low-density polyethylene (LLDPE), can lay flat against each other and are sealed along common edge 548 to form a tube or conduit between the panels. At one end 556 of liner 508, panels 540 and 544 and seal 552 form a pouch 560 adapted to collect and store pumped milk. In another embodiment, end 556 is not sealed, and the milk is allowed to drain out of liner 508, e.g., into a glass or plastic container (not shown). Also, another embodiment includes pleats on the sides and bottom of pouch 560 to increase the total volume of milk pouch 560 can hold. Above pouch 560 is rib and groove seal 564, by the use of which the user can seal pumped milk within pouch 560. Liner 508 has a portion 568 of decreasing width, terminating in a narrow portion 572 sized to fit flat within the gap between rigid downward sloping wall 512 of rigid member 496 and flexible downward sloping wall 516 of flexible member 500 of valve 504, valve 504 impinging against liner 508 to prevent reverse milk flow back into suction chamber 492 during pumping. Valve 504 can also close more generally around liner 508 to prevent the flow of air around liner 508 into suction chamber 492 during pumping. Above narrow portion 572 liner 508 has a gradually widening portion 576, shaped to conform to portion 580 of suction bell 488 nearest breast shield 532. Above gradually widening portion 576 is a sharply widening portion 584, shaped to conform to the contour of breast shield 532. Above sharply widening portion 584 is narrowing portion 588 which can be stretched around and past rim 520 of breast shield 532, so that liner 508 stays in place when a woman's breast is placed into breast shield 532 against liner 508. The two sheets 540 and 544 that comprise the initially flat liner can be partially or completely separate (no edge seal) above sharply widening portion 584, and when liner 508 is installed within pump 476, tabs 596 and 600 can be grasped, parted, and pulled past opposite sides of breast shield rim 520. Predefined frangible parting line 592 allows tab portions 596, 600 of narrowing portion 588 to be torn away from the remainder of narrowing portion 588 after liner installation. Also, predefined frangible parting line 604 enables sealable pouch portion 560 of liner 508 to be separated from the remainder of liner 508 above rib and groove seal 564. This allows pouch 620 to be separated cleanly without cutting, making handling of pumped milk easier, and facilitating refrigerated storage of pumped milk.

Figure 19:
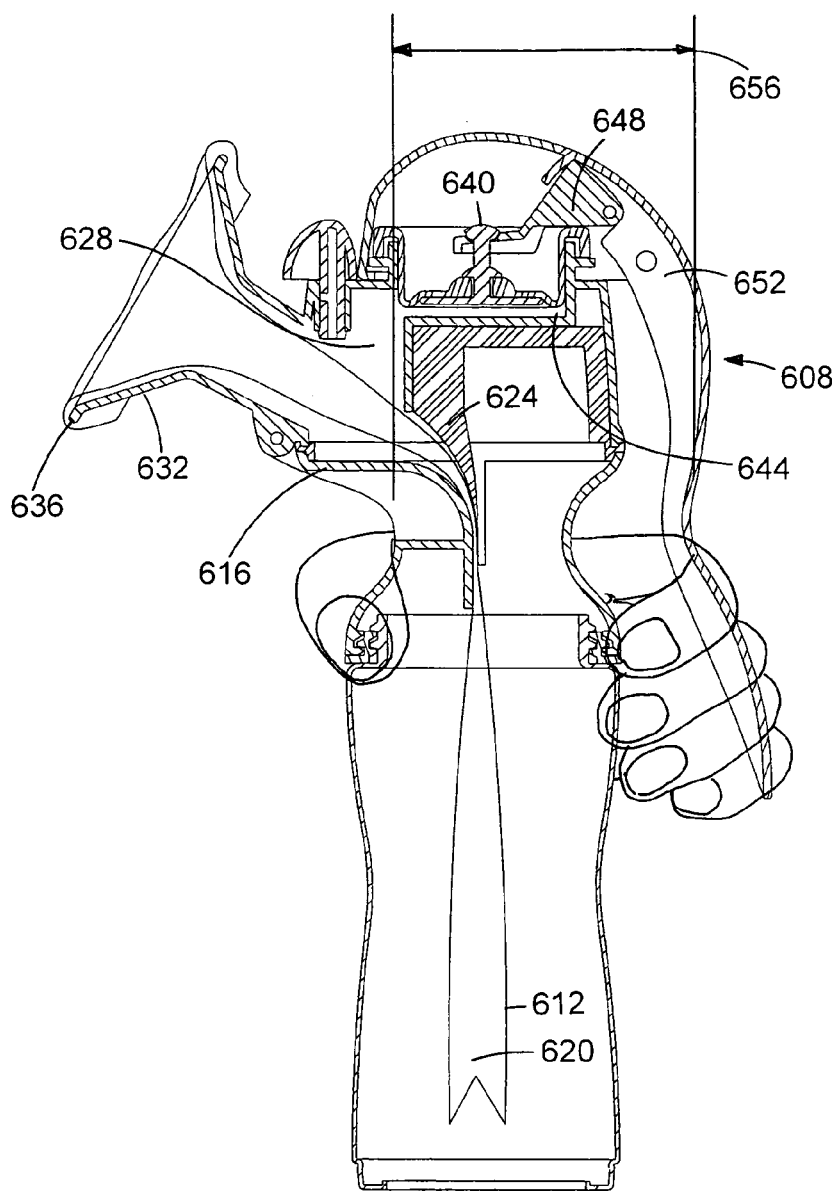
FIGS. 19 and 20 illustrate the breast pump with the pumping lever at its extended and retracted positions, respectively.
Figure 20:
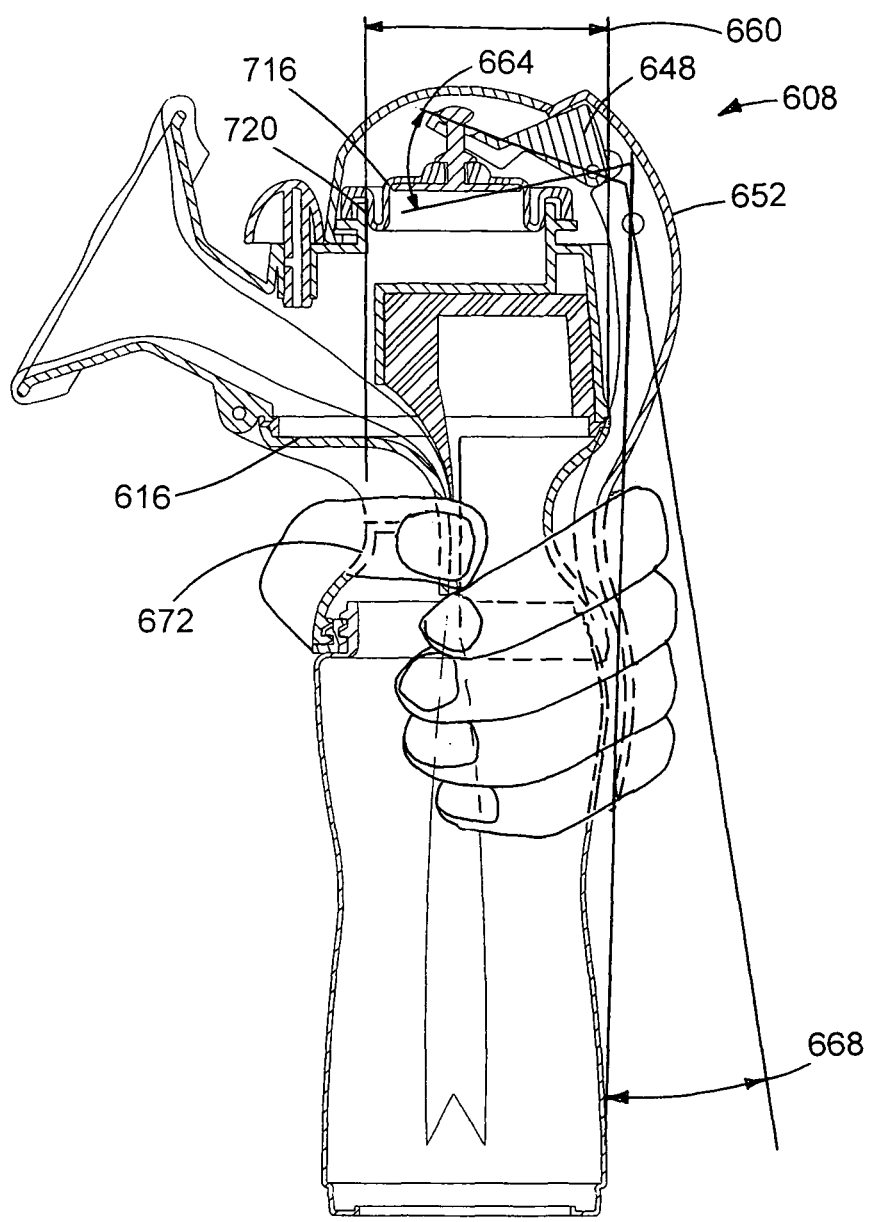

Referring to FIGS. 19 and 20, manual breast pump 608 is shown. Liner 612 extends upward through suction bell 616 from below where it forms a pouch 620, which is pleated for larger storage volume. Liner 612 extends through valve 624, through suction chamber 628, into and through breast shield 632, and to and around edge 636 of breast shield 632, thus shielding all parts of breast pump 608 from contamination from pumped milk. The user can operate two pumping levers 648 and 652 in concert to retract plunger 620 through a cylinder 644 and outward of suction chamber 628. The user moves primary lever 648 through essentially the same angle or arc as pumping lever 216 of FIGS. 1 and 2, since primary lever 648 is designed to move plunger 640 about the same distance through cylinder 644 as does pumping lever 216 of FIGS. 1 and 2. However, the interface between primary lever 648 and gripping lever 652 can comprise a linkage which provides a mechanical advantage of less than one, i.e., a linkage which enables a user to cause primary lever 648 to rotate through the required arc 664 (i.e., the arc corresponding to the distance of retraction of plunger 640 that is required for creation of an adequate cyclic vacuum), by urging gripping lever 652 through an arc 668 that is smaller than arc 664. From the perspective of the user, this can be advantageous. The required squeezing distance or "throw" of pump 608 can be defined as the difference between grip length 656 as measured when gripping lever 652 is at its fully extended position, and grip length 660 as measured when gripping lever 652 is at its forward-most or fully retracted position (i.e., dimension 656 minus dimension 660). Reducing the required throw can make cyclic pumping action more comfortable. For the sake of comparison, grip length of pump 2 of FIGS. 1 and 2 can range from 74 millimeters when pumping lever 216 is at its fully-extended position, to 52 millimeters when end 218 of pumping lever 216 has been urged as far toward suction bell 8 as the mechanism permits (i.e., the fully retracted position), covering a rotation angle for pumping lever 216 of thirty degrees. This corresponds to a squeezing distance of 22 millimeters. The grip length of manual breast pump 608, by contrast, can range from a dimension 656 corresponding to a fully extended 75 millimeters to a dimension 660 corresponding to a fully retracted 56.8 millimeters, corresponding to a squeezing distance of 18.2 millimeters, and covering a rotation angle for the gripping lever 652 of only fifteen degrees (lower than that of pump 2 because the rotational linkage between gripping 652 and primary 648 levers includes a 1:2 mechanical advantage). The squeezing distance or throw of pump 608 is thus 17.3% lower than that of pump 2. This can have the advantage of reducing fatigue over the many vacuum cycles necessary when pumping breast milk. Additionally, a neck about suction bell 616 provides a recess 672 on the opposite side of suction bell 616 from gripping lever 652, allowing the grip widths represented by dimensions 656 and 660 to be reasonably small, contributing to the comfort of women using pump 608, and reducing the incidence of fatigue.

With continued reference to FIGS. 19-20, a flexible member (e.g., liner 612) is coupled to the outer edge 636 of the breast shield 632 and extends into the breast shield 632. The suction chamber 628 is defined between the flexible member and the breast shield 632 thereby isolating the human breast from hydraulic communication with the suction chamber 628. When a vacuum pump cyclically evacuates air from the suction chamber 628 via the conduit 432 (as illustrated in FIG. 1), the flexible member deforms or moves toward an inner surface of the breast shield 632.

It will be understood that various modifications may be made without departing from the spirit and scope of the invention. For example, a two-piece milk drainage valve similar to valve 504 of pump 476 (as shown in FIG. 15) can be used in place of valve 36 of pump 2 (as shown in FIG. 1). Accordingly, other embodiments are within the scope of the following claims.

What is claimed is:

1. A breast pump comprising:
    a suction bell including
        a breast shield having an outer edge and an inner edge and being sized to receive a human breast, the breast shield including a longitudinal axis and a vertically oriented conduit through a wall of the breast shield, the conduit being arranged transverse to the longitudinal axis of the breast shield, the conduit including a longitudinal axis;
    a flexible member coupled to the outer edge of the breast shield and extending into the breast shield, the flexible member defining therethrough a pathway for receiving the human breast and pumped milk;
    a suction chamber defined between the flexible member and the breast shield, the suction chamber isolated from hydraulic communication with the human breast;
    a vacuum cycling pump in hydraulic communication with the conduit and suction chamber through a length of flexible tubing, such that operation of the vacuum pump cyclically evacuates air from the suction chamber causing cyclic deformation of the flexible member towards an inner surface of the breast shield in response to the air evacuation, thereby decreasing the volume of the suction chamber and reducing pressure in the pathway, the flexible member inhibiting hydraulic communication between the pathway and the vacuum pump;
    a container positioned to receive and contain the pumped milk, the container including a longitudinal axis; and
    a removable valve separate from the flexible member, the removable valve being disposed at a lower end of the suction bell, between the pathway and the container and adapted to drain pumped milk from the human breast to the container, and
    wherein the longitudinal axis of the vertically oriented conduit is parallel to the longitudinal axis of the container.

2. The breast pump of claim 1, wherein the valve comprises a duckbill valve.

3. The breast pump of claim 1 wherein the flexible member is removable.

4. The breast pump of claim 1 wherein the flexible member defines an inner volume for receiving the human breast, and wherein the inner volume increases in response to the evacuation of air from the suction chamber.

5. The breast pump of claim 1 wherein the flexible member comprises a flexible plastic liner.

6. The breast pump of claim 5 wherein the container comprises a separable extension of the liner defining a pouch external to the suction bell for containing pumped milk.

7. The breast pump of claim 6, wherein the liner includes a frangible section for separating the pouch from a remainder of the liner for milk storage.

8. The breast pump of claim 7, wherein the liner includes a pouch seal below the frangible section, for sealing milk within the pouch for milk storage.

9. The breast pump of claim 1, wherein the pump is manually operable.

10. The breast pump of claim 9, wherein the pump includes a manually operable pump lever secured to the suction bell for cyclical motion with respect thereto to generate a cyclical vacuum within the suction chamber.

11. A breast pump comprising:
    a suction bell defining a compartment, the suction bell including
        a rigid receptacle having a first end and a second end and being sized to receive a human breast, the rigid receptacle including a longitudinal axis, and
        a conduit oriented transverse to the longitudinal axis, the conduit having a passageway through a wall of the rigid receptacle and a longitudinal axis;
    a flexible membrane releasably coupled to the first end of the receptacle, the flexible membrane having an internal surface adapted for contact with the human breast and, an external surface spaced from the receptacle to define a chamber;
    a pump in hydraulic communication with the chamber through the conduit, such that operation of the pump cyclically evacuates air from the chamber causing cyclic deformation of the flexible membrane in response to the air evacuation, the flexible membrane inhibiting hydraulic communication between the human breast and the vacuum pump;
    a removable valve separate from the flexible membrane, the removable valve being positioned at a lower portion of the suction bell and adapted to receive pumped milk and allow the pumped milk to flow therethrough; and
    a container at least partially positioned below the valve and adapted to receive the pumped milk, the container including a longitudinal axis, and
    wherein the longitudinal axis of the conduit is parallel to the longitudinal axis of the container.

12. The breast pump of claim 11, wherein the pump includes a lever coupled to the suction bell for cyclical motion with respect thereto to generate a cyclical vacuum within the chamber.

13. The breast pump of claim 11 wherein the flexible membrane defines an inner volume for receiving the human breast, and wherein the inner volume increases in response to the evacuation of air from the suction chamber.

14. The breast pump of claim 11, wherein the pump is manually operable.

15. The breast pump of claim 11 wherein the container is positioned within a second container.

16. The breast pump of claim 11 wherein the pump is electrically controlled.

17. The breast pump of claim 11 wherein the container includes a frangible section for separating a portion of the container for storage.

18. The breast pump of claim 17 wherein the container includes a seal below the frangible section for sealing milk within the container for storage.

19. The breast pump of claim 11 further comprising a pathway for the milk from the human breast to an aperture at the lower portion of the suction bell.

20. The breast pump of claim 19 wherein the valve is positioned within the aperture.

21. The breast pump of claim 19 wherein the valve is coupled to the aperture.

22. A breast pump comprising:
a rigid receptacle sized to receive a human breast, the receptacle including a longitudinal axis and a conduit including a longitudinal axis oriented transverse to the longitudinal axis of the receptacle;
a flexible membrane releasably coupled to a first end of the receptacle and extending into the receptacle, an external surface of the flexible membrane and an internal surface of the receptacle defining a chamber;
a suction bell coupled to a second end of the receptacle opposite the first end;
a pathway adapted to receive pumped milk and to deliver the milk from the human breast to an aperture at a lower portion of the suction bell;
a pump in hydraulic communication with the chamber through the conduit, such that operation of the pump cyclically evacuates air from the chamber causing cyclic deformation of the flexible membrane in response to the air evacuation, the flexible membrane inhibiting hydraulic communication between the pathway and the vacuum pump;
a removable one-way valve separate from the flexible membrane, the removable valve being coupled to the lower portion of the suction bell and adapted to allow the pumped milk to flow therethrough;
a base integral with the lower portion of the suction bell and including a plurality of threads adapted to receive a corresponding container; and
a liner positioned below the valve, supported by the container and adapted to receive the pumped milk, and
wherein the container includes a longitudinal axis oriented parallel to the longitudinal axis of the conduit.

23. The breast pump of claim 22, wherein the pump includes a lever coupled to the suction bell for cyclical motion with respect thereto to generate a cyclical vacuum within the chamber.

24. The breast pump of claim 22 wherein the container includes a frangible section for separating a portion of the container for storage.

25. The breast pump of claim 24 wherein the container includes a seal below the frangible section for sealing milk within the container for storage.

26. The breast pump of claim 22 wherein the container is positioned within a second container.

27. The breast pump of claim 22 wherein the valve is positioned within the aperture.

28. The breast pump of claim 22 wherein the valve is coupled to the lower portion of the suction bell.

29. The breast pump of claim 22 wherein the pump is electrically controlled.

30. The breast pump of claim 22 wherein the flexible membrane defines an inner volume for receiving the human breast, and wherein the inner volume increases in response to the evacuation of air from the suction chamber.

31. The breast pump of claim 22, wherein the pump is manually operable.

32. A breast pump comprising:
a receptacle having an end sized to receive a human breast, the receptacle having a longitudinal axis;
a first conduit extending through a wall of the receptacle, the first conduit having a longitudinal axis arranged transverse to the longitudinal axis of the receptacle;
a flexible membrane coupled to the end of the receptacle, the flexible membrane extending into the receptacle for receiving pumped milk from the human breast;
a suction chamber defined between the flexible membrane and an interior surface of the receptacle, the suction chamber isolated from hydraulic communication with the human breast received in the receptacle;
a pump in hydraulic communication through the first conduit with the suction chamber, wherein operation of the pump cyclically evacuates air from the suction chamber causing cyclic deformation of the flexible membrane in response to the air evacuation;
a container positioned to receive the pumped milk, the container including an opening through which to receive the pumped milk and the container having a longitudinal axis; and
a second conduit positioned to direct the pumped milk from the human breast to the container, wherein the second conduit is narrower than the opening of the container and at least a portion of the second conduit has a longitudinal axis parallel to the longitudinal axis of the container.

33. The breast pump of claim 32 wherein the flexible membrane is removable.

34. The breast pump of claim 32 wherein the flexible membrane comprises a flexible plastic liner.

35. The breast pump of claim 32, wherein the pump is manually operable.

36. The breast pump of claim 32 wherein the pump is electrically controlled.

37. The breast pump of claim 32, wherein the pump is in communication with the suction chamber through a length of flexible tubing.

* * * * *